United States Patent
Truong-Le et al.

(10) Patent No.: US 8,293,275 B2
(45) Date of Patent: Oct. 23, 2012

(54) SPRAY FREEZE DRY OF COMPOSITIONS FOR PULMONARY ADMINISTRATION

(75) Inventors: Vu Truong-Le, Campbell, CA (US); Binh V. Pham, Mountain View, CA (US); John F. Carpenter, Littleton, CO (US); Theodore W. Randolph, Niwot, CO (US); Robert Seid, Chapel Hill, NC (US)

(73) Assignees: Med Immune, LLC, Gaithersburg, MD (US); The Regents of the University of Colorado, Boulder, CO (US)

( * ) Notice: Subject to any disclaimer, the term of this patent is extended or adjusted under 35 U.S.C. 154(b) by 23 days.

(21) Appl. No.: 12/807,343

(22) Filed: Sep. 1, 2010

(65) Prior Publication Data

US 2010/0330162 A1    Dec. 30, 2010

Related U.S. Application Data

(62) Division of application No. 10/412,644, filed on Apr. 10, 2003, now Pat. No. 7,923,029.

(60) Provisional application No. 60/372,242, filed on Apr. 11, 2002.

(51) Int. Cl.
*A61K 9/14* (2006.01)

(52) U.S. Cl. ............... 424/489; 424/450; 435/235.1; 435/170

(58) Field of Classification Search ............... None
See application file for complete search history.

(56) References Cited

U.S. PATENT DOCUMENTS

| | | | |
|---|---|---|---|
| 2,845,368 A | 7/1958 | Fredrickson | |
| 5,290,765 A | 3/1994 | Wettlaufer et al. | |
| 5,585,112 A | 12/1996 | Unger et al. | |
| 5,639,441 A | 6/1997 | Sievers et al. | |
| 5,902,844 A | 5/1999 | Wilson | |
| 5,932,245 A | 8/1999 | Wunderlich et al. | |
| 6,136,346 A | 10/2000 | Eljamal et al. | |
| 6,187,330 B1 * | 2/2001 | Wang et al. | 424/426 |
| 6,258,341 B1 | 7/2001 | Foster et al. | |
| 6,268,053 B1 | 7/2001 | Woiszwillo et al. | |
| 6,284,282 B1 * | 9/2001 | Maa et al. | 424/499 |
| 6,309,671 B1 | 10/2001 | Foster et al. | |
| 6,342,251 B1 | 1/2002 | Illum et al. | |
| 2003/0202978 A1 * | 10/2003 | Maa et al. | 424/184.1 |

FOREIGN PATENT DOCUMENTS

WO    WO 01/93829 A2    12/2001

OTHER PUBLICATIONS

Wolkers et al., "From Anhydrobiosis to Freeze-Drying of Eukaryotic Cells," Comparative Biochemistry and Physiology—Part A; Molecular & Integrative Physiology, vol. 131, Issue 3 pp. 535-543 (2002).

Mm et al., "Biopharmaceutical Powders: Particle Formation and Formulation Considerations", Current Pharmaceutical Biotechnology, vol. 1, No. 3, pp. 283-302 (2000).

* cited by examiner

*Primary Examiner* — Mary E Mosher
*Assistant Examiner* — Myron Hill
(74) *Attorney, Agent, or Firm* — Gary Baker; Quine Intellectual Property Law Group, P.C.

(57) ABSTRACT

This invention provides methods and compositions to preserve bioactive materials, such as viruses, bacteria, cells, or liposomes, in freeze dried particles suitable for pulmonary administration. Methods provide spray freeze drying of formulations to form stable freeze dried particles.

29 Claims, 7 Drawing Sheets

Fig. 2

B/Harbin CAZ039 Stability in AVS43SF1004B

Slope: -0.076 log FFU/mL/month
Time for 1 log loss: 13 months

Solid line: linear fit curve
Dotted lines: 95% confidence bands

Virus Potency (log FFU/mL) vs Months at 25 °C

Fig. 7

B/Harbin CAZ039 Stability in AVS53SF1V

Slope: -0.015 log FFU/mL/day
Time for 1 log loss: 67 days

Solid line: linear fit curve
Dotted lines: 95% confidence bands

Days at 37 °C

Virus Potency (log FFU/mL)

SPRAY FREEZE DRY OF COMPOSITIONS FOR PULMONARY ADMINISTRATION

CROSS-REFERENCE TO RELATED APPLICATIONS

This application is a Divisional application claiming priority to and benefit of a prior to parent application 10/412,644, "Spray Freeze Dry of Compositions for Pulmonary Administration", by Vu Truong-Le, filed Apr. 10, 2003, which parent application claims priority to and benefit of a prior U.S. Provisional Application No. 60/372,242, "Method of Spray Freeze Drying Therapeutic Agents for Pulmonary Administration", by Vu Truong-Le, et al., filed Apr. 11, 2002. The full disclosure of the prior application is incorporated herein by reference.

FIELD OF THE INVENTION

The present invention is in the field of preservation of biologic materials in storage. In particular, the invention relates to, e.g., preservation of bioactive molecules in glassified matrices of spray freeze dried powder particles for delivery by the pulmonary route.

BACKGROUND OF THE INVENTION

Biological materials, such as proteins, peptides, nucleic acids, bacteria, cells, antibodies, enzymes, serums, vaccines, liposomes, and viruses, are generally unstable when stored in media or other liquid solutions. For example, enveloped viruses such as live influenza virus manufactured from egg allantoid fluid loose one log of potency, defined as Tissue Culture Infectious Dose (TCID50), in less than two to three weeks when stored under refrigerated temperature, i.e. approximately 4° C. At room temperature conditions (approximately 25° C.) and at warmer temperatures such as 37° C., the virus looses the such potency in a matter of days to hours, respectively. Bulk lyophilization processes, where aqueous formulas are frozen into solid blocks then dried by sublimation, are commonly used to stabilize these biological materials. Spray-drying is another process commonly used to remove water from biological materials to provide stability in storage. Substitution of protectant molecules, such as carbohydrates, after removal of water can increase stability by preventing chemical degradation, denaturation, and growth of microbial contaminants.

In lyophilization (freeze-drying), the biological material is commonly mixed as a solution or suspension with protective agents, frozen, and dehydrated by sublimation and secondary drying. The low temperatures of freezing and drying by sublimation can slow the kinetics of degradation reactions, but prolonged secondary drying processes carried out at elevated temperatures are often required to reduce residual moisture to an acceptable level. Moreover, freeze dried cakes must be laboriously ground and sized to a small and narrow size range if administration by inhalation is desired.

Lyophilization and secondary drying processes, as commonly practiced, can force a cell, virus, or biomolecule to undergo significant chemical and physical degradation. Degradation can be the loss of protein activity due to concentration of salts, precipitation/crystallization, shear stress, pH extremes, and residual moisture remaining through the freeze-drying. Freeze-drying can damage internal cell structures with ice crystals, fail to protect these compartments with stabilizer molecules, and destroy the bioactivity of internal molecules.

The formation of powder particles by grinding of lyophilized cakes or by spray drying is of substantial interest and importance to the biopharmaceutical industry for preservation and administration of biologically active materials. Not only can such fine particles provide a convenient storage form for biomaterials such as cells, viruses, proteins, non-protein biomolecules (including for example, DNA, RNA, lipids, and carbohydrates), but they can be substantially dehydrated for long-term storage, and rewettable for administration of the biomaterial for its intended use after the storage period. Such dried fine particles can be produced in a controlled diameter range and administered as a dried aerosol power, for example, via the pulmonary route, where the respiratory tract mucosa can rewet and dissolve the biomaterial in a patient. Numerous other uses of such fine and microfine particles containing a biomaterial are found in the art of pharmaceutics, biologics, and particularly in the field of live virus vaccines. Thus, it would be advantageous to develop methods of forming stable, specifically sized particles containing biologically active materials.

Spray drying is a well known process long used, e.g., in the food processing industry. For example, liquid products, such as milk, are sprayed through a nozzle into a stream of hot gasses to produce a powder. The increased surface area exposed in the spray mist, in combination with the high temperatures of the drying gas, can provide rapid removal of water from the liquid product. However, such process conditions are often unsuitable for sensitive biologic materials due to the shear stress, heat stress, oxidative stress, and conformational changes that can occur with loss of hydration water at high temperatures. There are several reports of spray drying therapeutic agents for pulmonary delivery, such as: Maa et al. J. Pharm. Sci. 87(2):152 (1998); Mumenthaler et al., Pharm. Res. 11(1):12 (1994); Chan et al., Pharm. Res. 14(2):431 (1997), PCT Publication No. WO 97/41833; U.S. Pat. No. 5,019,400 and WO 90/13285; Yeo et al., Biotechnology and Bioengineering 41:341 (1993) and Winters et al., J. Pharm. Sci. 85(6):586 (1996). Some of the problems encountered in spray drying pharmaceutical compositions are addressed in U.S. Pat. No. 5,902,844, Spray Drying of Pharmaceutical Formulations Containing Amino Acid-Based Materials, to Wilson. In Wilson, peptides in solution with a water soluble polymer are sprayed into a stream of drying gas to form a pharmaceutical composition. The presence of the polymer can protect the peptide from degradation by coating the peptide against chemical attacks and by substituting for water of hydration lost during drying. Certain sensitive peptides and other biological materials, such as nucleic acids, bacteria, cells, antibodies, enzymes, serums, vaccines, liposomes, and viruses can still be damaged, however, by the heat, shear stress and dehydration of the processes described by Wilson, and the like.

The heat and stress of bulk freeze drying and common spray drying can be reduced by spray freeze drying methods. For example, in U.S. Pat. No. 6,284,282, Methods for Spray Freeze Drying Proteins for Pharmaceutical Administration, to Maa et al., formulations of therapeutic proteins are atomized to into droplets that are frozen by immersion in a cold fluid before annealing and lyophilization to form particles with a physical size of from 6 um to 8 um. The particles formed by this method can be suitable for delivery of the therapeutic protein by pulmonary administration. Spray freeze drying can reduce shear stress by preparing particles with a small aerodynamic diameter from droplets with a larger physical diameter. Spray freeze drying can reduce heat stress by processing formulations in a cold environment and by providing a surface to volume ratio favorable to quick drying. However, the Maa methods are limited to protein therapeutics for pulmonary administration.

Drugs in the form of powder particles can be administered by inhalation. Inhalation therapy involves the administration of a drug in an aerosol form to the respiratory tract and includes both intranasal administration (via the upper respiratory tract including the nasal mucosa) and pulmonary administration (via the lower respiratory tract). Several means have been developed to deliver compounds directly to the passages of the lung or nose (see, pending application "Spray Freeze Dry of Compositions for Intranasal Administration", by Vu Truong-Le, et. al., attorney's reference 26-000910US, filed Apr. 10, 2003, full disclosure of which is incorporated herein by reference). The most common form, especially for water-insoluble drugs, is a powder suspension that is propelled into the mouth while the patient inhales. The pulmonary deposition efficiency of powder aerosols is influenced by several factors including physical shape and size, density, porosity, and flow patterns during delivery. The particle size distribution of the aerosolized drug compositions is very important to the therapeutic efficacy of the drug when delivered by inhalation. In spray freeze drying, the size of the liquid droplet is predictive of the powder particle size such that it is often possible to control the size distribution of the powder by controlling that of the droplets. Studies of inhaled aerosols indicate that particles or droplets of greater than about 20 micrometers in mean aerodynamic diameter are effectively excluded from entry into the lungs and are captured in the nasal-pharyngeal passages. Thus, the drug compounds to be delivered to the lung are usually formulated in such a way that the median aerodynamic diameter is below about 10 micrometers. In addition, even smaller particle sizes, on the order of 0.5 to 2.5 micrometers, are needed if the drug is to reach the alveolar sacs deep in the lungs.

A need remains for methods to preserve sensitive biological materials, such as proteins and live viruses in storage, particularly at temperatures above freezing. Methods to spray freeze dry a variety of bioactive materials, including cells, viruses, bacteria and liposomes, under low shear stress conditions, for stable storage, and/or for delivery by the pulmonary route are desirable in the fields of medicine and scientific research. The present invention provides these and other features that will become apparent upon review of the following.

SUMMARY OF THE INVENTION

The present invention includes, e.g., compositions of bioactive materials in stable porous particles and methods for preparation of the particles for administration of the particles by the pulmonary route. The methods include preparation of liquid formulations with the bioactive material, spray freezing the formulation to form frozen droplets, lyophilizing the droplets to form stable powder particles ranging in physical size from about 0.5 um to about 20 um, and recovery of the particles for storage or administration. Compositions of the invention include freeze dried particles prepared by the methods of the invention. Compositions of the invention include cells, bacteria, viruses and/or liposomes in dried particles having an average aerodynamic diameter between about 0.5 um and 10 um, and an average physical diameter between about 0.5 um and 20 um.

The methods of the invention generally include preparation of spray freeze dried particles for pulmonary administration by, e.g., spraying a liquid formulation of virus, bacteria, cells and/or liposomes to form droplets, freezing the droplets by immersion in a cold fluid to prepare frozen droplets, annealing the frozen droplets, drying the droplets to form powder particles, and recovering particles with an average physical diameter ranging from about 0.5 um to about 20 um, or from about 1 um to about 10 um, or from about 3 um to about 5 um, or about 3 um. The method can include, e.g., annealing the frozen droplets to a temperature the glass transition temperature of the frozen droplets before drying below (e.g., below about −10° C.). Viruses in the formulation can usefully include, e.g., influenza virus, parainfluenza virus, respiratory syncytial virus, human metapneumovirus, herpes simplex virus, cytomegalovirus, corona virus family members, SARS (severe acute respiratory syndrome) virus, Epstein-Barr virus, and/or the like. Bioactive materials can be diafiltered, ultrafiltered, concentrated, and/or buffer exchanged during preparation of the liquid formulation. For example, the bioactive material can be incorporated into the liquid formulation at a concentration ranging from about 5 pg/ml to about 75 mg/ml. The freeze dried particles produced can preferably have an average size of about 3 um.

Spraying of the formulations can be by any of several techniques known in the art. For example, spraying can be by common moderate pressure spraying (e.g., 50 psi), supercritical spraying (e.g., by admixture with near supercritical carbon dioxide), high pressure spraying (above about 200 psi), atomization (pre or post nozzle mixture with an atomizing gas), and/or the like. Spraying can be by ejecting the liquid formulation from a multifluid atomization assembly, a high pressure nozzle, an ultrasonic nozzle, slinging the formulation from a rotating disk, and/or the like.

The liquid formulation used in the methods of the invention can include, e.g., a polyol, a polymer, and/or a surfactant. For example, the polyol can be sucrose, trehalose, sorbose, melezitose, raffinose, mannitol, xylitol, erythritol, threitol, stachyose, sorbitol, glycerol, fructose, mannose, maltose, lactose, arabinose, xylose, ribose, rhamnose, galactose, glucose, L-gluconate, and/or the like. The polymer can be, e.g., dextran, human serum albumin (HSA), nonhydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, hydrolyzed gelatin, and/or the like. The surfactant can be, e.g., a polyethylene glycol sorbitan monolaurate (e.g., Tween 20), a polyoxyethylenesorbitan monooleate (e.g., Tween 80), a block copolymer of polyethylene and polypropylene glycol (e.g., Pluronic), and/or the like.

The sprayed formulation droplets can be frozen in a fluid of cold liquid or gas. The cold fluid can be, e.g., a gaseous or liquid form of argon, air, or nitrogen. The cold fluid can have a temperature preferably ranging from about −40° C. to about −200° C. The liquid droplets can have an average physical (MMD) diameter ranging from about 0.5 um to about 20 um, or from about 1 um to about 10 um.

The frozen droplets can be dried to form porous powder particles. Before primary drying by lyophilization, the frozen droplets can be annealed, e.g., by raising the temperature of the frozen droplets to less than about the glass transition temperature of the frozen droplets. The annealing temperature can be, e.g., less than about −10° C., or less than about −15° C. Lyophilization (freeze-drying) can proceed on application of a vacuum (pressure less than atmospheric) to the droplets to form powder particles by sublimation of water. Lyophilization proceeds more readily when a vacuum less than about 400 mTorr, or less than 200 mTorr, is applied.

The method of the invention provides for secondary drying of the lyophilized particles to remove residual moisture and increase stability of the particles. In one embodiment, the secondary drying temperature ranges from about 0° C. to about 50° C. A typical secondary drying temperature, as measured for an inlet drying gas, is about 35° C.

The powder particles can be administered, e.g., to a mammal in a therapeutically effective amount, such as bioactive material doses ranging from less than about 0.1 ng/kg to about 50 mg/kg. Optionally, the powder particles can be reconstituted and injected as a solution or suspension.

The present invention includes compositions of particles containing bioactive materials for pulmonary administration. The compositions of the invention can be prepared by a process of spraying a liquid formulation of the bioactive material, such as a virus, bacteria, cell, or liposome, to form droplets, freezing the droplets by immersion in a cold fluid to prepare frozen droplets, annealing the frozen droplets, drying the frozen droplets to form freeze dried powder particles, and recovering particles with an average physical size ranging from about 0.5 um to about 20 um. In an aspect of the invention, the compositions include, e.g., dried particles have an average aerodynamic particle size ranging from about 0.5 um to about 10 um, and an average physical diameter ranging from about 0.5 um to about 20 um, and contain a virus, bacteria, cell and/or liposome. Such particles can penetrate substantially into the pulmonary tract on inhalation by a patient. In one embodiment, compositions are prepared from liquid formulations comprising a live virus, about 40 weight percent sucrose, about 5 weight percent gelatin, and about 0.02 weight percent block copolymer of polyethylene and polypropylene glycol.

The bioactive material in the formulation can be, e.g., biological molecules, viruses, and/or cells. For example, the bioactive materials can be viruses, bacteria, cells, liposomes, and/or the like, present in the formulation in an amount less than about 10 weight percent, less than about 1 weight percent, or commonly with viruses, in an amount less than about 0.01 weight percent. Typical viruses included in the composition bioactive materials of the invention include, e.g., influenza virus, parainfluenza virus, respiratory syncytial virus, human metapneumovirus, herpes simplex virus, cytomegalovirus, SARS virus, corona virus family members, and Epstein-Barr virus. Particle compositions of viruses are often processed from liquid formulations with the virus present in an amount ranging from about $10^3$ $TCID_{50}$/mL to about $10^{12}$ $TCID_{50}$/mL, or from about $10^6$ $TCID_{50}$/mL to about $10^9$ $TCID_{50}$/mL. Dried powder particle compositions of the invention can provide virus present in an amount, e.g., from about $10^1$ $TCID_{50}$/g to not more than about $10^{12}$ $TCID_{50}$/g. Dried powder particle compositions can provide virus present in an amount, e.g., of about $10^1$ $TCID_{50}$/g, about $10^2$ $TCID_{50}$/g, about $10^3$ $TCID_{50}$/g, about $10^4$ $TCID_{50}$/g, about $10^5$ $TCID_{50}$/g, about $10^6$ $TCID_{50}$/g, about $10^7$ $TCID_{50}$/g, about $10^8$ $TCID_{50}$/g, about $10^9$ $TCID_{50}$/g, about $10^{10}$ $TCID_{50}$/g, or about $10^{11}$ $TCID_{50}$/g.

The compositions of the invention can be prepared from liquid formulations containing a polyol, a polymer additive, and/or a surfactant. Such ingredients can, e.g., provide protection to the bioactive material, structural stability, enhanced solubility, and other desirable characteristics to the compositions.

Polyols of the compositions can be present in the liquid formulation in an amount, e.g., ranging less than about 40 weight percent, from about 1 weight percent to about 20 weight percent, or from about 10 weight percent to about 5 weight percent. The polyols can include, e.g., sucrose, trehalose, sorbose, melezitose, raffinose, mannitol, xylitol, erythritol, threitol, sorbitol, glycerol, fructose, mannose, maltose, lactose, arabinose, xylose, ribose, rhamnose, galactose, glucose, L-gluconate, and/or the like.

Polymers of the compositions can include, e.g., dextran, human serum albumin (HSA), hydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, nonhydrolyzed gelatin, and/or the like. Hydrolyzed gelatin can have a molecular weight ranging, e.g., between about 1 kDa and about 50 kDa, or about 3 kDa.

Surfactants of the compositions can be present in the liquid formulations in amounts ranging from about 0.001 weight percent to about 2 weight percent. The surfactants can be, e.g., alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, polyacrylates, acrylic acid graft copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes, lignin-sulfite waste liquor, alkyl phosphates, quaternary ammonium compounds, amine oxides, betaines, and/or the like.

The compositions can include other ingredients, such as a pH buffer, other drugs, bulking agents, and/or sustained release polymers. Buffers of the compositions can include, e.g., potassium phosphate, sodium phosphate, sodium acetate, sodium citrate, histidine, imidazole, sodium succinate, ammonium bicarbonate, and/or a carbonate, to maintain pH at between about pH 3 to about pH 8, or about pH 7.2. Other drugs, useful in the compositions of the invention, can include, e.g., aids to penetration, decongestants, bronchiole relaxers, expectorants, analgesics, and the like. Bulking agents can include, e.g., lactose, mannitol, and/or hydroxyethyl starch (HES). Sustained release semi-permeable polymer matrix of the compositions can include, e.g., polylactides, copolymers of L-glutamic acid and gamma-ethyl-L-glutamate, poly(2-hydroxyethyl methacrylate, or liposomes.

The freeze dried powder particle compositions of the invention can have an average aerodynamic particle size ranging, e.g., from about 0.2 um to about 10 um, from about 0.5 um to about 5 um, or about 3 um, with a moisture content of ranging from about 1 weight percent to about 5 weight percent. The particles can contain, e.g., sucrose or trehalose in an amount ranging from about 10 weight percent to about 95 weight percent. Such particles can protect bioactive materials so they can remain stable in storage at about 25° C. for about 1 year or more, or at 4° C. for more than about 2 years.

DEFINITIONS

It is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" can include mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

"Ambient" temperatures or conditions are those at any given time in a given environment. Typically, ambient room temperature is approximately 22° C., ambient atmospheric pressure, and ambient humidity are readily measured and will vary depending on the time of year, weather conditions, altitude, etc.

"Buffer" refers to a buffered solution that resists changes in pH by the action of its acid-base conjugate components. The pH of the buffer will generally be chosen to stabilize the active material of choice, and will be ascertainable by those in the art. Generally, this will be in the range of physiological pH, although some proteins, can be stable at a wider range of pHs, for example acidic pH. Thus, preferred pHs range are from about 1 to about 10, with from about 3 to about 8 being particularly preferred; more preferably, from about 6.0 to about 8.0; yet more preferably, from about 7.0 to about 7.4; and most preferably, at about 7.0 to about 7.2. Suitable buffers include, e.g., a pH 7.2 phosphate buffer and a pH 7.0 citrate buffer. As will be appreciated by those in the art, there are a large number of suitable buffers that may be used. Suitable buffers include, but are not limited to, potassium phosphate, sodium phosphate, sodium acetate, sodium citrate, sodium succinate, histidine, imidazole, ammonium bicarbonate and carbonate. Generally, buffers are used at molarities from about 1 mM to about 2 M, with from about 2 mM to about 1 M being preferred, and from about 10 mM to about 0.5 M being especially preferred, and 25 to 50 mM being particularly preferred.

"Degassing" refers to the release of a gas which has been dissolved in a liquid when the partial pressure of the gas in solution is greater than the applied pressure. If water is exposed to nitrogen gas at one atmosphere (about 760 Torr), and the partial pressure of nitrogen in the water equilibrates to the gas phase pressure, nitrogen can bubble from the water if the gas pressure is reduced. This is not boiling, and can often occur at pressures above a pressure that would result in boiling of the solvent. For example, bottled carbonated soft drinks, with a high partial pressure of $CO_2$ gas, bubble rapidly (without boiling of the water) when pressure is reduced by removing the bottle cap.

"Dispersibility" means the degree to which a powder composition can be dispersed (i.e. suspended) in a current of air so that the dispersed particles can be respired or inhaled into the respiratory tract of a subject. Thus, a powder that is only 20% dispersible means that only 20% of the mass of particles can be suspended for inhalation into the respiratory tract.

"Dry" in the context of spray freeze dried particle compositions refers to residual moisture content less than about 10%. Dried compositions are commonly dried to residual moistures of 5% or less, or between about 3% and 0.1%. "Dry" in the context of particles for inhalation can mean that the composition has a moisture content such that the particles are readily dispersible in an inhalation device to form an aerosol.

"Excipients" generally refer to non-active agent compounds or materials that are added to ensure or increase the stability of the therapeutic agent during the spray freeze dry process and afterwards, for long term stability and flowability of the powder product, to provide desirable physical characteristics to the powder, and the like. Suitable excipients generally provide relatively free flowing particulate solids, are basically innocuous when inhaled by a patient and do not significantly interact with the therapeutic agent in a manner that alters its biological activity. Suitable excipients are described below and include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof.

"Glass" or "glassy state" or "glassy matrix," refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion but have very slow (almost immeasurable) rotational and translational components. As a metastable system, it is stable for long periods of time when stored well below the glass transition temperature. Because glasses are not in a state of thermodynamic equilibrium, glasses stored at temperatures at or near the glass transition temperature relax to equilibrium and lose their high viscosity. The resultant rubbery or syrupy, flowing liquid is often chemically and structurally destabilized. While a glass can be obtained by many different routes, it appears to be physically and structurally the same material by whatever route it was taken. The process used to obtain a glassy matrix for the purposes of this invention is generally a solvent sublimation and/or evaporation technique.

The "glass transition temperature" is represented by the symbol $T_g$ and is the temperature at which a composition changes from a glassy or vitreous state to a syrup or rubbery state. Generally $T_g$ is determined using differential scanning calorimetry (DSC) and is standardly taken as the temperature at which onset of the change of heat capacity (Cp) of the composition occurs upon scanning through the transition. The definition of $T_g$ is always arbitrary and there is no present international convention. The $T_g$ can be defined as the onset, midpoint or endpoint of the transition; for purposes of this invention we will use the onset of the changes in Cp when using DSC and DER. See the article entitled "Formation of Glasses from Liquids and Biopolymers" by C. A. Angell: Science, 267, 1924-1935 (Mar. 31, 1995) and the article entitled "Differential Scanning Calorimetry Analysis of Glass Transitions" by Jan P. Wolanczyk: Cryo-Letters, 10, 73-76 (1989). For detailed mathematical treatment see "Nature of the Glass Transition and the Glassy State" by Gibbs and DiMarzio: Journal of Chemical Physics, 28, NO. 3, 373-383 (March, 1958). These articles are incorporated herein by reference.

"Penetration enhancers" are generally surface active compounds that promote penetration of a drug or other bioactive material through a mucosal membrane or tissue lining and are generally used in the respiratory tract, gastrointestinal tract, intranasally, intrarectally, and intravaginally.

"Pharmaceutically acceptable" excipients (vehicles, additives) are those which can reasonably be administered to a subject mammal to provide an effective dose of the active ingredient employed. Preferably, these are excipients which the Federal Drug Administration (FDA) have to date designated as 'Generally Regarded as Safe' (GRAS).

"Pharmaceutical composition" refers to preparations which are in such a form as to permit the biological activity of the active ingredients to be unequivocally effective, and which contain no additional components which are toxic as administered to the subjects.

A "polyol" is a substance with multiple hydroxyl groups, and includes sugars (reducing and nonreducing sugars), sugar alcohols and sugar acids. Preferred polyols herein have a molecular weight which is less than about 600 kDa (e.g. in the range from about 120 to about 400 kDa). A "reducing sugar" is a polyol which contains a hemiacetal group that can reduce metal ions or react covalently with lysine and other amino groups in proteins. A "nonreducing sugar" is a sugar which does not have these properties of a reducing sugar. Examples of reducing sugars are fructose, mannose, maltose, lactose, arabinose, xylose, ribose, rhamnose, galactose and glucose. Nonreducing sugars include, e.g., sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof.

"Powder" means a composition that consists of solid particles that are relatively free flowing and capable of being readily dispersed in an inhalation device and subsequently inhaled by a patient so that the particles are suitable for intranasal or pulmonary administration via the upper respiratory tract including the nasal mucosa.

"Recommended storage temperature" for a composition is the temperature ($T_s$) at which powdered drug composition is to be stored to maintain the stability of the drug product over the shelf life of the composition in order to ensure a consistently delivered dose. This temperature is initially determined by the manufacturer of the composition and approved by the governmental agency responsible for approval the composition for marketing (e.g., the Food and Drug Administration in the U.S.). This temperature will vary for each approved drug product depending on the temperature sensitivity of the active drug and other materials in the product. The recommended storage temperature will vary from about −70° C. to about 40° C., but powdered drug compositions are generally recommended for storage between about 4° C. and about 25° C. Usually a drug product will be kept at a temperature that is at or below the recommended storage temperature.

A biologically active material "retains its biological activity" in a pharmaceutical composition, e.g., if the biological activity of the biologically active material, such as a monoclonal antibody in a liposome, at a given time is within about 10% (within the errors of the assay) of the biological activity exhibited at the time the pharmaceutical composition was prepared as determined in a binding assay, for example. In the case of living viruses and bacteria, biological activity can be considered retained when the viral titer or colony count of the composition is within one log of the initial value. For live eukaryotic cells, the biological activity can be considered retained when the live cell count of the composition is within 50% of the initial count. The assay that can be used to determine live influenza virus titer is the Fluorescent Focus Assay (FFA assay). The titer from this assay is reported as Log Fluorescent Focus Unit per milliliter (Log FFU/ml). One Log FFU/ml is approximately equal to one Log Tissue Culture Infectious Dose per ml (Log TCID50/ml). Other "biological activity" assays are elaborated below.

A biologically active material "retains its chemical stability" in a pharmaceutical composition, if, e.g., the chemical stability at a given time is such that the biologically active material is considered to still retain its biological activity as defined above. Chemical stability can be assessed by detecting and quantifying chemically altered forms of the biologically active material. Chemical alteration can involve size modification (e.g. clipping of proteins) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

A biologically active material "retains its physical stability" in a pharmaceutical composition if, e.g., it shows no significant aggregation, precipitation and/or denaturation upon visual examination of color and/or clarity, or as measured by UV light scattering or by size exclusion chromatography.

"Spray freeze dried" as used herein means that the composition is prepared by spray freeze drying. Spray freeze drying is a process conceptually a hybrid of spray drying and freeze drying, in that an aqueous solution or suspension of the therapeutic agent, termed herein the "liquid formulation", is introduced via a nozzle, spinning disk or an equivalent device to spray the solution into fine droplets. The liquid formulation is preferably a solution, although suspensions, slurries or the like may be used as long as it is substantially homogeneous to ensure uniform distribution of the therapeutic agent in the formulation and ultimately in the powdered composition. In spray freeze drying, the spray mist of droplets can be immersed into a cold fluid, either a liquid or a gas, at a temperature below the freezing point of the aqueous solvent of the pre-spray freeze dry formulation. Spraying the formulation into the cold fluid can result in the rapid freezing of the fine droplets to form frozen droplets. The frozen droplets can be collected, and the solvent can be removed, generally through sublimation (i.e., lyophilization) in a vacuum. As discussed below, the particles can be annealed (i.e. the temperature adjusted to a temperature less than the glass transition temperature of the frozen droplets) prior to drying. This can produce a spray freeze dried powder having particles with a desired size range and characteristics, as is more fully discussed below. Suitable spray freeze drying methodologies are also described below.

A "stable" formulation or composition is one in which the biologically active material therein essentially retains its physical stability, chemical stability, and/or biological activity upon storage. Various analytical techniques for measuring stability are available in the art and are reviewed, e.g., in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. Trend analysis can be used to estimate an expected shelf life before a material has actually been in storage for that time period. For live influenza viruses, stability is defined as the time it takes to loose 1 log of potency, expressed either as fluorescence focus units, i.e. FFU/ml or as tissue culture infectious dose, i.e. TCID50/ml. These values are determined by conducting the fluorescence focus assay (FFA) or Tissue Culture Infectious Dose (TCID50) assay. Preferably, the composition is stable at room temperature (~25° C.) or at 40° C. for at least 1 month, and/or stable at about 2-8° C. for at least 1 year. Furthermore, the composition is preferably stable following freezing (to, e.g., −70° C.) and thawing of the composition.

"Near supercritical spray drying", as used herein, refers to removal of a solvent, such as water, from a liquid formulation comprising mixture with a near supercritical fluid (see, e.g., pending application "Preservation of Bioactive Materials by Spray Drying", by Vu Truong-Le, et. al., attorney's reference 26-001110US, filed Apr. 10, 2003, full disclosure of which is incorporated herein by reference). The supercritical spray drying can include, e.g., dissolution of the solvent from the liquid formulation into the supercritical fluid, spraying of the liquid formulation by the force of supercritical fluid pressure, and/or expansion or degassing of the supercritical fluid from a mixture with the liquid formulation to disrupt it into fine droplets. Significant water can be removed during the expansion, and/or the resultant particles or droplets can be further dried with a dry gas stream or in a vacuum chamber. Many supercritical fluids such as, for example, supercritical carbon dioxide, may be used in the supercritical drying process.

"Near supercritical fluid" refers to a fluid held at, or within about 10%, of a critical point pressure and/or temperature. A critical point is a combination of temperature and pressure wherein a substance can no longer exist as a liquid if the temperature (critical temperature) is increased or the pressure (critical pressure) is lowered. The critical temperature is the temperature above which a gas cannot be liquefied; the temperature above which a substance cannot exhibit distinct gas and liquid phases for a given pressure. The critical pressure is the pressure required to liquefy a gas (vapor) at a critical temperature. For example, the critical pressure and temperature of carbon dioxide are 74 atmospheres and 31 degrees Centigrade, respectively. Carbon dioxide held at a pressure and temperature above its critical point is in a supercritical condition or state. Critical pressures and temperatures for other substances are provided below:

| Fluid | Pc (bar) | Tc (° C.) |
| --- | --- | --- |
| Carbon dioxide | 74 | 31 |
| Nitrous oxide | 72 | 36 |
| Sulfur hexafluoride | 37 | 45 |
| Xenon | 58 | 16 |
| Ethylene | 51 | 10 |
| Chlorotrifluoromethane | 39 | 29 |
| Ethane | 48 | 32 |
| Trifluoromethane | 47 | 26 |

In a pharmacological sense, a "therapeutically effective amount" of a biologically active material refers to an amount effective in the prevention or treatment of a disorder wherein a "disorder" is any condition that would benefit from treatment with the biologically active material. This includes chronic and acute disorders or diseases including those pathological conditions which predispose a patient to the disorder in question.

"Treatment" refers to both therapeutic treatment and prophylactic or preventative measures. Those in need of treatment include those already with the disorder as well as those in which the disorder is to be prevented.

"Unit dosage" refers to a receptacle containing a therapeutically effective amount of a composition of the invention.

BRIEF DESCRIPTION OF THE DRAWINGS

FIG. 2 shows the stability of influenza virus B/Harbin which has been formulated as AVS43SF. The time for 1 log loss in virus potency at 25° C. is 13 months.

FIG. 7 shows the stability of influenza virus B/Harbin which has been formulated as AVS53SF. The time for 1 log loss in virus potency at 37° C. is 67 days.

DETAILED DESCRIPTION

Figure 1:
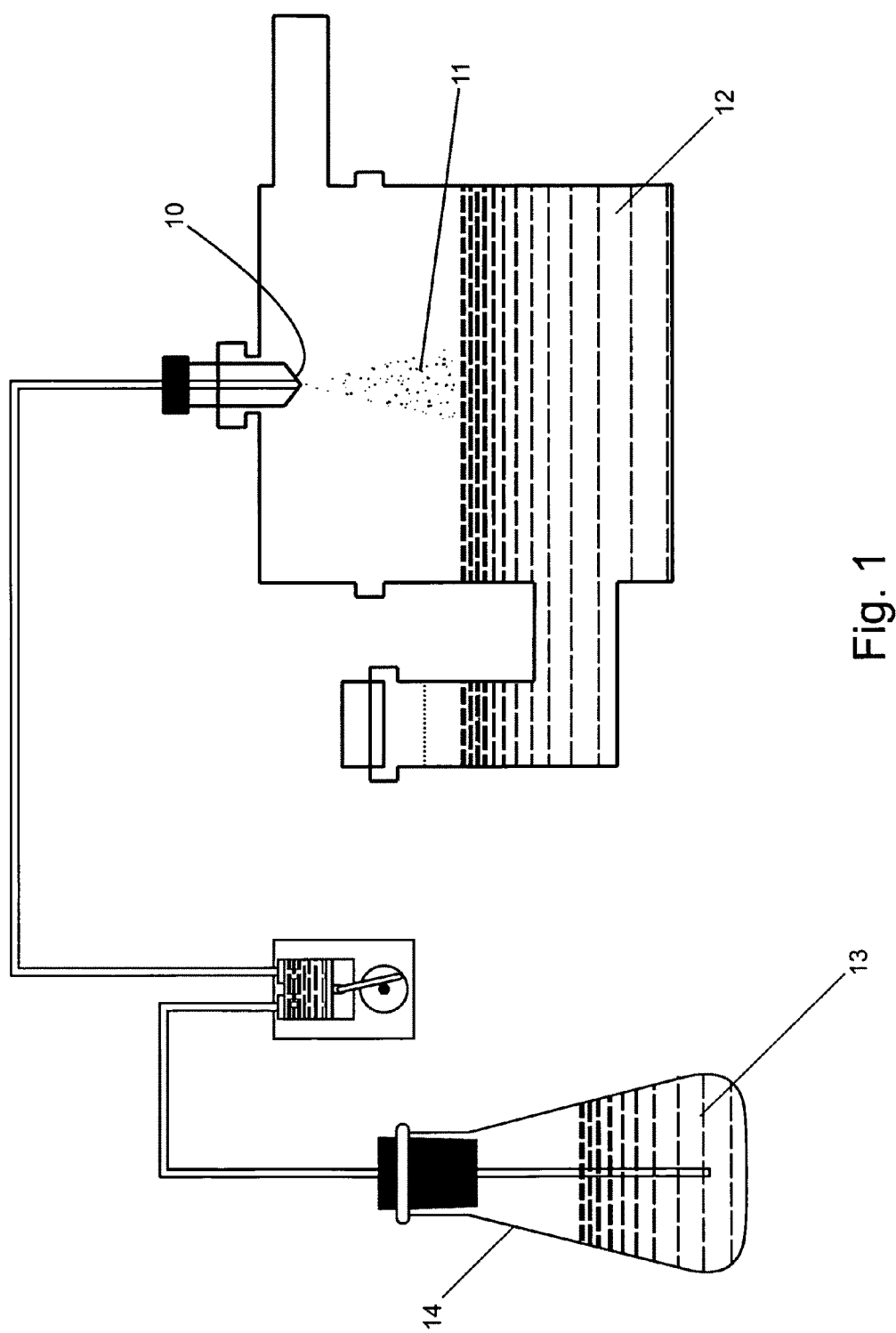
FIG. 1 shows a schematic diagram of a spray/freeze apparatus.

The methods and compositions of the present invention can provide, e.g., high initial purity, extended storage, and effective pulmonary administration of bioactive materials, such as viruses, bacteria, cells and/or liposomes, encased in a glassy matrix of freeze dried powder particles. The method provides, e.g., formulation of the bioactive material with a polyol and/or bulking agent, spraying the formulation into a cold fluid to produce frozen droplets, recovery, and lyophilization of the frozen droplets to produce 0.5-20 um freeze dried powder particles suitable for pulmonary administration of the bioactive material. Compositions of the invention can be produced, e.g., by the methods of the invention. Compositions of the invention can be, e.g., dried particles of viruses, bacteria, cells, and/or liposomes with aerodynamic particle size from about 0.5 um to about 10 um and with a physical size from about 0.5 um to about 20 um.

Methods of Preparing Particles for Pulmonary Administration

Methods of the invention can include, e.g., preparation of a liquid formulation of a bioactive material, spraying the formulation to form droplets, freezing the droplets by immersion into a cold fluid, annealing the frozen droplets, primary water removal by sublimation, secondary drying of the particles, recovery of freeze dried particles, and pulmonary administration of the bioactive material by inhalation of the particles. The aqueous liquid formulation can contain, e.g., a bioactive material, a polyol, a polymer, and/or a surfactant. Spraying can be, e.g., by conventional spraying, high pressure spraying, supercritical spraying, atomization, and/or the like. Rapid freezing of droplets can be, e.g., by immediate immersion of spray droplets in liquid nitrogen or a stream of cold gas. Primary drying of the frozen droplets can be, e.g., by lyophilization. Secondary drying can be by, e.g., continued freeze drying with higher temperatures in the vacuum chamber, contact exposure to temperature controlled surfaces, or by suspension of particles in a vortex or fluidized bed of temperature/humidity controlled gas. The dried powder particle product can be recovered, e.g., by settling after sizing.

The methods of the invention can provide compositions of high purity with beneficial reconstitution properties. Droplets with a certain physical diameter can be sprayed to prepare freeze dried particles with a significantly lower aerodynamic diameter (i.e., freeze dried particles can be less dense, e.g., a density less that about 0.9, or less than about 0.7, less that about 0.4, or less than about 0.2 g/cc). The relationship between physical geometric particle size and aerodynamic size is determined mostly by particle's density; however, parameters such as rugosity, shape, porosity could be influential as well. However, in general, the aerodynamic size is equal to the geometric (physical) size multiplied by the square root of the particle's density. In addition, the porous freeze dried particles can be reconstituted, e.g., more rapidly, at higher concentrations, and/or in fluids with higher osmolality (e.g., respiratory tract mucus), than conventionally spray dried particles of the same mass.

Preparing a Liquid Formulation

Liquid formulations of the invention can include, e.g., a bioactive material formulated with a polyol, polymer, surfactant, an amino acid, and/or buffer, in an aqueous solution. The ingredients can be combined in a sequence using techniques appropriate to the constituents, as is appreciated by those skilled in the art. For example, a bioactive material, such as a virus or bacterium, can be, e.g., concentrated and separated from growth media by centrifugation or filtration before mixture with a polyol solution to form a suspension. Antibodies can be purified and concentrated, e.g., by affinity chromatography before dissolving into a solution with other formulation ingredients. Liquid formulations for spray freeze drying can be prepared by mixing the bioactive material, polyols, and other excipients, in an aqueous solution. Some bioactive materials, such as, e.g., peptides and antibodies, can dissolve readily into an aqueous solution. Other bioactive materials, such as, e.g., bacteria and liposomes, can be particles that exist as a suspension in a solution. Whether the bioactive material provides a solution or suspension, it is often necessary, e.g., to avoid severe conditions of shear stress or temperature when mixing them into a formulation for spray freeze drying. Where some formulation constituents require heat or strong stirring to bring into solution, they can, e.g., be dissolved separately, then gently blended with the bioactive material after cooling.

The bioactive materials of the invention can be, e.g., industrial reagents, analytical reagents, vaccines, pharmaceuticals, therapeutics, and the like. Bioactive materials of the invention include, e.g., bacteria, cells, liposomes, viruses, and/or the like. The bioactive material can be, e.g., living cells and/or viable viruses. The bioactive material can be, e.g., nonliving cells, viruses, or liposomes useful as vaccines or delivery vehicles for therapeutic agents. Viral bioactive materials of the invention can be, e.g., live viruses such as, influenza virus, parainfluenza virus, respiratory syncytial virus, herpes simplex virus, cytomegalovirus, SARS virus, human metapneumovirus, corona virus family members, Epstein-Barr virus, and/or the like. Preparation steps for liquid formulations of these materials can vary depending on the unique sensitivities of each bioactive material.

The concentration of bioactive material in the liquid formulation can vary widely, depending, e.g., on the specific activity, concentration of excipients, route of administration, and/or intended use of the material. Where the bioactive material is a vaccine, live virus or bacteria, for example, the required concentration of material can be quite low. Where the bioactive material is, e.g., a pharmaceutical in a liposome, or viable cells for storage and later culture, the required concentration can be higher. In general, bioactive materials can be present in the liquid formulations of the invention at a concentration, e.g., between less than about 1 pg/ml to about 150 mg/ml (15 weight percent), from about 0.1 ng/ml to about 50 mg/ml, or about 10 mg/ml.

In some embodiments of the invention, bioactive materials can be, e.g., concentrated and/or exchanged into a liquid formulation solution. Such processes can, e.g., remove residual components from the bioactive material in purification processes and guarantee the proportion of liquid formulation constituents. Concentration can be, e.g., by centrifugation, filtration, or ultrafiltration to concentrations of from less than about 1 ug/ml to about 100 mg/ml, from about 5 mg/ml to about 75 mg/ml, from about 10 mg/ml to about 60 mg/ml, or from about 20 mg/ml to about 60 mg/ml. Buffer exchange can be, e.g., by dialysis, diafiltration, centrifugation and dilution, and/or the like.

The liquid formulation of bioactive materials can optionally include, e.g., any of a variety of polyols. In the methods of the invention, polyols can provide, e.g., a viscosity enhancing agent to reduce the effects of shear stress during spraying. The polyols can provide protective barriers and chemistries to the freeze dried powder particles of the invention. For example, the polyol, such as sucrose, can physically surround and protect the bioactive material from exposure to damaging light, oxygen, moisture, and/or the like. The polyols can, e.g., replace water of hydration lost during drying, to prevent denaturation of biomolecules of the material. Although the invention is not limited to any particular polyols, the liquid formulations, and freeze dried powder particle compositions, can include, e.g., sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, stachyose, sorbitol, glycerol, L-gluconate, and/or the like. Where it is desired that the formulation be freeze-thaw stable, the polyol can be one which does not crystallize at freezing temperatures (e.g. $-20°$ C.) such that it destabilizes the biologically active material in the formulation; however, in many embodiments of the methods, freezing is very rapid (e.g., >1000° C./min) so that freezing can occur before crystal formation processes have progressed significantly. The amount of polyol used in the formulation can vary depending on the nature of the biologically active material, other excipients, and intended use. However, the liquid formulations generally include a nonreducing sugar in a concentration between about 1% and 40%; more preferably, between about 1% and 20%, between about 1% and 10%, or about 5% by weight. In a particularly preferred embodiment, the liquid formulation comprises about 10% sucrose.

Polymers can be included in the liquid formulations of the method, e.g., to provide protective and structural benefits. As with polyols, polymers can provide, e.g., physical and chemical protection to the bioactive materials. The linear or branching strands of polymers can provide, e.g., increased structural strength to the particle compositions of the invention. Polymers can be applied as a protective and/or time release coat to the outside of freeze dried particles of the invention. Many polymers are, e.g., highly soluble in water, so they do not significantly hinder, and often aid, reconstitution of freeze dried particles. Polymer protective agents, in the methods of the invention can include, e.g., dextran, human serum albumin (HSA), nonhydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, hydrolyzed gelatin, and/or the like. Preferably, hydrolyzed gelatin is used with a molecular weight of between about 1,000 and 50,000 Daltons (Da), or about 3,000 Da. Generally, the concentration of polymer in a liquid formulation is, e.g., from about 0.5% to about 10%; more preferably, between about 1 and 5%. A preferred formulation comprises about 5% hydrolyzed gelatin by weight The liquid formulation of the invention can include, e.g., a surfactant compatible with the particular bioactive material involved. A surfactant can enhance solubility of other formulation components to avoid aggregation or precipitation at higher concentrations. Surface active agents can, e.g., lower the surface tension of the liquid formulation so to minimize denaturation of bioactive materials at gas-liquid interfaces, and/or so that finer droplets can be formed at lower pressures during spraying. The liquid formulations according to the invention comprise between about 0.001% and 2%; and preferably, between about 0.01% and 1%, or about 0.2%, of a nonionic surfactant, an ionic surfactant, or a combination thereof.

Buffers can be added to the formulations of the method, e.g., to provide a suitable stable pH to the formulations of the method and compositions of the invention. Typical buffers of the invention include, e.g., potassium phosphate, sodium phosphate, sodium acetate, sodium citrate, histidine, glycine, sodium succinate, histidine, imidazole, ammonium bicarbonate, and/or a carbonate. The buffers can be adjusted to the appropriate acid and salt forms to provide, e.g., pH stability in the range from about pH 3 to about pH 10, from about pH 4 to about pH 8. A pH near neutral, such as, e.g., pH 7.2, is preferred for many compositions.

Other excipients can be included in the formulation. For example, amino acids, such as arginine and methionine can be constituents of the formulation and compositions. The amino acids can, e.g., act as zwitterions that can neutralize charged groups on protein-protein surfaces, as well as processing surfaces and storage containers, preventing nonspecific binding of bioactive materials. The amino acids can increase the stability of compositions by, e.g., scavenging oxidation agents, scavenging deamidation agents, and stabilizing the conformations of proteins. In another example, glycerol can be included in the formulations of the invention, e.g., to act as a polyol and/or plasticizer in the freeze dried particle compositions. EDTA can be included in the composition, e.g., to reduce aggregation of formulation constituents and/or to scavenge metal ions that can initiate destructive free radical chemistries.

Spraying and Freezing Droplets

The liquid formulations of the methods can be sprayed into a mist of droplets in a spray chamber and rapidly frozen in a cold fluid. Spraying can be by any technique known by those skilled in the art, such as atomization (e.g., spraying liquid admixed with a jet of gas), spraying from a nozzle, flinging from a spinning disk, mixing with a near supercritical gas and ejection from a supercritical nozzle, high pressure spraying, ejection from an ultrasonic nozzle, and/or the like. The spray mist can be frozen in a cold fluid, such as a liquefied gas or very cold gas, as will be described in detail below. Frozen droplets can be collected in a tank attached in some orientation to the spray chamber; preferably, the spray chamber is positioned above the collection tank sharing a common space. Preferably the collection tank and the spray chamber are made of a material which can withstand the temperatures and gas pressures experienced in carrying out the process. A suitable material is, for example, stainless steel.

Typical spraying techniques include moderate pressure spraying and atomization. Liquid formulations of moderate viscosity (i.e., near that of water) can be sprayed from a nozzle at pressures of about 10 psi to about 200 psi to form a mist of droplets. In atomization, a stream of gas, such as air, can be mixed with a spray of liquid formulation in a nozzle or just outside a nozzle, e.g., to initiate drying, disrupt droplets into smaller sizes, and/or to transport the droplets in a desired direction. Pressure for spraying can be generated, e.g., by pumping the formulation, or by application of a pressurized gas to a chamber holding the formulation. In one aspect of the invention, for example, liquid formulation is sprayed from a nozzle having a 100 um internal diameter orifice by pumping at a pressure of about 80 psi with atomization, to provide droplets with an average size of less than about 10 um.

In a typical embodiment of atomized spraying, the liquid formulation can flow under pressure through a multifluid atomization nozzle assembly to be ejected into a spray of formulation droplets. The multifluid atomization assembly can include a spray head adapter into which the liquid formulation and atomization gas can be introduced through separate conduits. The atomization gas can be, e.g., any gas which does not react with the dispersed system undergoing multifluid atomization. Examples of suitable atomization gasses include, but are not limited to, air, nitrogen, carbon dioxide, and argon. The atomization nozzle assembly can include separate fluid caps and air caps. Examples of suitable multifluid atomization nozzles include, but are not limited to, external air (or gas) atomizers (e.g., Glatt Model 014 available from Ortho Liquid System, NC, Models SUE15A; SU2A and SU2 available from Spray Systems Co., Wheaton, Ill.), internal air atomizers (e.g., SU12; Spray Systems Co). The atomization nozzle can have an air cap with an inner diameter ranging from $64 \times 10^{-3}$ to $120 \times 10^{-3}$ inch. Typically, a $70 \times 10^{-3}$ air cap is used. Conventional spray drying equipment can be used, such as Buchi, Niro Yamato, Okawara, Kakoki, and the like. In certain spray processes, such as, e.g., near supercritical spraying, the nozzle can be wrapped with heating tape, to prevent freezing in the nozzle head.

In high pressure spraying techniques of the invention, the liquid formulation can include viscosity enhancing agents to allow spraying at higher pressures without undue degradation of bioactive materials from shear stress (see, pending application "High Pressure Spray-Dry of Bioactive Materials", by Vu Truong-Le, et. al., U.S. Provisional Application No. 60/434,377, filed Dec. 17, 2002, full disclosure of which is incorporated herein by reference). For example, the liquid formulation can be sprayed from a nozzle at a pressure effective in providing the desired droplet size. Higher pressures generally provide, e.g., smaller droplet sizes. Where the formulation is more viscous, e.g., a higher pressure can be required to provide the desired droplet size. In the presence of a surfactant, e.g., a less high pressure can be required to provide the desired droplet size. The high pressure spraying pressures of the invention can be, e.g., between about 200 psi and about 2500 psi, between about 500 psi and 1500 psi, or about 1000 psi.

Near supercritical spraying of the liquid formulation is another aspect of the methods of the invention. For example, a liquid formulation of the invention can be mixed in a chamber with a near supercritical fluid before spraying through a capillary restrictor nozzle outlet to form a fine mist of droplets. Without being bound to a particular theory, the combination of near supercritical fluid with the liquid formulation can provide an emulsion mixture of droplets saturated and/or surrounded with fluid under pressure. As the mixture is released from the spray nozzle, the pressure drops rapidly allowing an explosive expansion, and/or effervescence (degassing), that disrupts the droplets into a fine mist. Such a mist can be, e.g., finer than would result with spraying at the same pressure without a near supercritical fluid. The droplets can experience, e.g., cooler temperatures and less shear stress than would result from spraying at a pressure high enough to provide the same fine droplets without a near supercritical fluid. Absorption of latent heat during expansion of near supercritical gasses can provide cold gases (fluid) to promote freezing of sprayed formulation droplets.

Liquid formulation droplets can be rapidly frozen by immersion in a cold fluid. The spray chamber can be provided with a conduit and nozzles for introduction of the freezing medium into the spray chamber. In one embodiment, the cold fluid is a cold gas, such as, e.g., air, carbon dioxide, nitrogen, or argon. According to a preferred embodiment of the invention, the freezing medium is a cryogenic fluid, for example, liquid nitrogen or liquid argon. Accordingly, the apparatus for spray freezing is manufactured from materials and according to a design compatible with the temperatures of the process. The liquid formulation can be atomized into droplets which freeze upon contact with the freezing medium. Sprayed droplets can be, e.g., sprayed down onto the surface of a cryogenic fluid where they will rapidly freeze due to the high surface to volume ratio of the droplets, rapid heat conductivity of the liquid and the extreme cold of the fluid, as shown in FIG. 1. Conventional spray drying equipment can be used, such as Buchi, Niro Yamato, Okawara, Kakoki and the like. The atomization conditions, including atomization gas flow rate, atomization gas pressure, liquid flow rate, etc., can be controlled to produce liquid droplets having a specific range of physical diameter (mass medium diameter—MMD) of from about 0.5 um to about 20 um, from 1 um to about 10 um, or from about 3 um to about 5 um. Alternately, the liquid formulation can be atomized into an ultracooled gas, such as ultracooled nitrogen gas or another inert gas. Generally, temperatures ranging from about −200° C. to −40° C. are used, with from about −200° C. to about −80° C. being preferred, and about −200° C. being more preferred.

Lyophilization

Frozen droplets can be lyophilized to produce, e.g., low density freeze dried particles with about the same physical diameter as the frozen droplets. In freeze drying (lyophilization) water is removed by sublimation under a vacuum (pressure less than atmospheric) to leave the bioactive material, excipients, residual buffers, solvents or salts, e.g., in a protective glassy matrix. Lyophilization can be accomplished in a variety of ways, as is known in the art. That is, techniques that can be used for traditional lyophilization (i.e. freezing as a cake rather than as droplets) can be applied to lyophilization of frozen droplets with little modification. For example, the cold fluid can be removed from the spray chamber and a vacuum applied. In one embodiment, frozen droplets in a slurry with cold fluid is, e.g., aliquoted to dosage vials before removal of the cold fluid and lyophilization in the vials. Alternately, the frozen droplets can be transferred to a specialized lyophilization chamber to be freeze dried. In one embodiment, a vacuum is applied at about the same temperature at which freezing occurred.

Optionally, the method includes an annealing step wherein the temperature of the frozen particles is raised above the temperature of the cold fluid prior to or during the application of the vacuum. Annealing can, e.g., increase thermal energy to accelerate sublimation without disrupting the glassy matrix. This can be done as one or more steps; that is, the temperature can be increased one or more times either before or during the drying step of the vacuum. Preferred annealing temperatures include an initial increase such that the vacuum of less than about 500 mTorr (preferably less than about 250 mTorr) is applied and the temperature is raised to less than about −10° C. to about −15° C.; and more preferably, the temperature can be raised to near or just below the glass transition temperature of the frozen particles. In a preferred embodiment, a vacuum of less than about 500 mTorr (more preferably, less than about 250 mTorr, or about 200 mTorr) can be applied while the droplets are maintained at a temperature of less than about −25° C., or about −40° C. Latent heat lost during sublimation can be replaced, e.g., by conduction of heat from the surface of the lyophilization chamber or from the gaseous environment.

Primary drying is complete, e.g., at the end of lyophilization. The residual solids of, e.g., bioactive material, polyols, polymers, and/or the like, can form a glassified matrix to protect the bioactive material and/or a stable porous structural matrix. As the porous matrix can substantially retain the physical dimensions of the frozen droplets, removal of the water can reduce the density, and aerodynamic diameter, of the particles.

Secondary Drying

In a preferred embodiment, a secondary drying step is performed after lyophilization. Secondary drying in this context means that additional water is removed to reduce the residual moisture of the particles. This is generally done at temperatures from about 0° C. to about 50° C., with from about 10° C. to about 40° C. being preferred, and about 35° C. being the most preferred. The particles can be secondarily dried for a period of time sufficient to remove the desired amount of water from the particles. The actual period of time will depend on the temperature, the strength of the vacuum, the size of the sample, etc. Generally, the particles are secondarily dried to a residual moisture from about 0.1% to 10% residual moisture; from about 0.5% to about 5% being preferred; or from about 0.5% to about 2%.

Secondary drying of the structurally stabilized and primarily dried particles can, e.g., remove entrapped solvent, residual moisture, and/or water of molecular hydration, to provide a composition of freeze dried particles that is stable in storage, e.g., for extended periods at ambient temperatures. Secondary drying can involve, e.g., suspension of particles in a vortex of drying gas, suspension of particles in a fluidized bed of drying gas, and/or application of warm temperatures to contained particles in a strong vacuum for several hours or days. The rapid drying of porous particles formed during spraying and lyophilization can allow reduced temperatures and reduced times for secondary drying in methods of the invention.

Secondary drying conditions can be used, e.g., to further lower the moisture content of freeze dried particles. Particles can be collected in a secondary drying chamber and held at a temperature between about 0° C. and about 50° C.; these temperatures can be cooler than typical secondary drying temperatures for lyophilized cakes due to the porosity and high surface area of freeze dried particles. The chamber can be maintained at a reduced pressure and secondary drying can continue, e.g., for about 2 hours to about 5 days, or about 2 hours to about 24 hours, until residual moisture is reduced to a desired level. Secondary drying can be accelerated by providing an updraft of drying gasses in the chamber to create a fluidized bed suspension of the freeze dried particles. Particles with lower residual moisture generally can show better stability in storage with time. Secondary drying can continue until the residual moisture of the freeze dried particles is between about 0.5 percent and about 10 percent, or less than about 5 percent. At very low residual moisture values, some bioactive molecules can be denatured by loss of water molecules of hydration. This denaturation can often be mitigated by providing alternative hydrogen binding molecules, such as sugars, polyols, and/or polymers, in the process liquid formulation.

The drying gas can be recycled and conditioned to provide desired drying conditions. The drying gas can be an inert gas, such as nitrogen, to avoid chemical degradation of the bioactive material during drying. The gas can be cycled from the secondary drying chamber, through desiccators or condensers to remove humidity, through heat exchangers to heat or cool the gas to provide the desired drying temperature, and recycled, e.g., back to the secondary drying chamber. An ion generator can inject ions into the stream of particles to reduce charge build up and/or to prevent agglomeration of fine particles into aggregates.

Freeze dried particles of the invention can have a size on drying, e.g., suitable for the handling, reconstitution, and/or administration requirements of the product. For example, freeze dried particles of bioactive materials for administration by deep pulmonary inhalation can be smaller, with a MMD physical size between about 0.5 um and about 10 um, compared to intranasal delivery by inhalation of particles with a size between about 20 um and about 150 um. The particle size for products that reconstitute slowly can be smaller to speed dissolution of the particles, or the initial liquid formulation can have fewer solids for a more porous particle. Spray freeze dried particles can have, e.g., a lower density, because ice can be removed from droplets without collapse of a cake structure supported by the remaining solids. Such particles can have, e.g., a physically larger size for inhaled administration due to their lower aerodynamic radius (e.g., up to about 20 um and still reaching pulmonary surfaces in significant amounts). Freeze-dried particles can, e.g., be larger than particles dried from liquid droplets and still retain quick reconstitution properties due to the porous nature of freeze-dried particles. Freeze dried particles of the invention for pulmonary delivery can have average physical diameters, e.g., between about 0.5 um and 25 um, between about 1 um and about 20 um, between about 3 um and 15 um or between about 5 um and about 7 um. Freeze dried particles of the invention can have an average aerodynamic particle size ranging from about 0.5 um to about 10 um, with from about 1 um to about 7 um, or from about 3 um to about 5 um.

During the secondary drying process, e.g., a spray coat or other protective coating can be applied to the freeze dried particles. For example, a mist of a polymer solution can be sprayed into a suspension of drying particles in a vortex or fluidized bed.

The methods of the invention can result, e.g., in a pharmaceutically-acceptable, glassy matrix freeze dried particles comprising at least one biologically active material within the amorphous glassy matrix. Preferably, the composition is almost completely dry. Some water or other aqueous solvent can remain in the composition but typically, not more than about 5% residual moisture remains by weight. The drying temperature can range from about 10° C. to about 70° C., about 25° C. to about 45° C., or about 35° C. A typical secondary drying process can include, e.g., raising the temperature to a drying temperature of from about 30° C. to about 35° C., and holding for from about 0.5 days to about 5 days to provide a stable dried powder composition with 0.1% to about 5%, or about 2% residual moisture. As used herein, "dry", "dried", and "substantially dried" encompass those compositions with from about 0% to about 5% water. Preferably, the glassy matrix will have a moisture content from about 0.1% to about 3% as measured using the Karl Fisher method.

The resulting product of spray freeze drying can be, although not exclusively, amorphous solid particles, wherein the glassy excipient material, e.g. sucrose, is in an amorphous glassy state and encases the biologically active material, thereby preventing protein unfolding and significantly slowing molecular interactions or cross-reactivity, due to greatly reduced mobility of the compound and other molecules within the glassy composition. This process has been postulated to occur either via mechanical immobilization of the protein by the amorphous glass or via hydrogen bonding to polar and charged groups on the protein, i.e. via water replacement, thereby preventing drying induced denaturation and inhibiting further degradative interactions. As long as the solid is at a temperature below its glass transition temperature and the residual moisture remaining in the excipients is relatively low, the labile proteins and/or bioactive material containing lipid membranes can remain relatively stable. It should be noticed that achieving a glassy state is not necessarily a prerequisite for long term stability as some bioactive materials can fare better in a more crystalline state. Mechanisms attributed to stabilization of biologicals can be multifactorial and not limited to the amorphous nature of the powder matrix in which the active ingredient is encased. Stabilization under the process described here can involve a number of factors including but not limited to the thermal history that the biomaterials is subjected to, the reduction in conformational mobility and flexibility of the protein side chains and/or reduction in the free volume as a result of the encasement, improvement in the structural rigidity of the matrix, reduction in the phase separation of excipient from the active ingredient, improvement in the degree of water displacement by selecting the optimal hydrogen bonding donor. The latter is a function of the affinity and avidity of the excipient for the surface of the protein, nucleic acids, carbohydrate, or lipids being stabilized. In general, as long as the solid is at a temperature below its glass transition temperature and the residual moisture remaining in the excipients is relatively low, the labile proteins and/or bioactive material containing lipid membranes can remain relatively stable.

Recovery of Bioactive Material in Freeze Dried Particles

Freeze dried particles of the invention can be recovered with desired activity and in a form suitable to the intended route of administration. In processes in which freeze drying takes place after aliquoting of frozen particles in a slurry of cold fluid, freeze dried particles of the invention can be physically recovered from single dose unit glass vials, from larger vessels that the original frozen slurry was dried in, such as pans (e.g. Lyogard™ trays), or bottles, or from other containers. When the process includes secondary drying in a gas stream or particle transfers in gas stream suspensions, recovery can be, e.g., by settling or filtration after drying. The methods of the invention can provide high recovery of active and stable material due to the moderate process conditions involved. Methods of the invention can provide, e.g., particles adapted for administration as pulmonary deposited particles.

Physical recovery of freeze dried particles can depend, e.g., on the amount of material retained or expelled by the spray-drying equipment, and losses incurred due to particle size selection methods. For example, material containing the bioactive material can be lost in the plumbing, and on surfaces of the spray-drying equipment. Solutions or particles can be lost in the process, e.g., when an agglomeration of spray droplets grows and falls out of the process stream, or when under sized droplets dry to minute particles that are carried by drying gasses through the secondary drying chamber in a process waste stream.

Freeze dried particles of a desired average size and size range, can be selected, e.g., by filtration, settling, the use of air classifiers, impact adsorption, and/or other means known in the art. Freeze dried particles can be sized by screening them through one or more filters with uniform pore sizes or by further size reduction using various forms of milling. Optionally, large particles can by separated by allowing them to fall from a suspension of particles in a moving stream of liquid or gas. Large particles can also impact and stick or fall from surfaces at the outside of a turning fluid stream while the stream carries away smaller or less dense particles. Smaller particles can be separated by allowing them to be swept away in a stream of liquid or gas moving at a rate at which larger particles settle.

Recovery of active bioactive material can be affected, e.g., by physical losses, cell disruption, denaturation, aggregation, fragmentation, oxidation, and/or the like, experienced during the spray-dry process. The recovery of bioactive material activity in the process is the product of the physical recovery times the specific activity of recovered material. The methods of the invention can offer improved recovery of bioactivity over the prior art, e.g., by providing spray dry techniques that reduce shear stress, reduce drying time, reduce drying temperatures, and/or enhance stability.

Administration of Bioactive Materials

Where it is appropriate, the bioactive material of the invention can be administered, e.g., to a mammal in a therapeutically effective amount. Bioactive materials of the invention can include, e.g., viruses, bacteria, cells, liposomes, and/or the like. Such materials can act as therapeutics, nutrients, vaccines, pharmaceuticals, prophylactics, and/or the like, that can provide benefits on administration to a patient, e.g., by inhalation to be deposited, dissolved and/or absorbed on lower respiratory tract including, e.g., pulmonary mucus membranes, bronchioles and alveoli. For example, freeze dried particles about 10 um, 1 um, or less, in aerodynamic diameter can be administered by pulmonary inhalation, where they can be removed from the air stream by contact with mucus membranes and/or gas exchange surfaces of the lung.

In a preferred embodiment, the bioactive material is a live attenuated influenza virus vaccine, cold viruses, SARS virus, corona virus family members, or variants thereof, and the disorder presents symptoms associated with the a cold or flu. The disorder being treated can be a combination of two or more of the above disorders. Those in need of treatment include those already with the disorder as well as those prone to having the disorder or diagnosed with the disorder or those in which the disorder is to be prevented. The treatment regime herein can be consecutive or intermittent or any other suitable mode. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature.

Bioactive materials of the invention can be administered by injection. The spray freeze dried particles can be administered directly under the skin of a patient using, e.g., a jet of high pressure air. More commonly, the freeze dried particles can be, e.g., reconstituted with a sterile aqueous buffer for injection through a hollow hypodermic needle. Such injections can be, e.g., intramuscular, intra venous (IV), subcutaneous, intrathecal, intraperitoneal, and the like, as appropriate. Freeze dried particles of the invention can be reconstituted to a solution or suspension with a bioactive material concentration, e.g., from less than about 1 pg/ml to about 500 mg/ml, or from about 5 ng/ml to about 400 mg/ml, or about 50 mg/ml, as appropriate to the dosage and handling considerations. Freeze dried particles of the invention can be reconstituted to a solution or suspension with a bioactive material concentration, e.g., greater than the bioactive material concentration of the initial liquid formulation. Reconstituted freeze dried particles can be further diluted, e.g., for multiple vaccinations, administration through IV infusion, and the like. In this embodiment, any number of known diluents can be used, as will be appreciated by those in the art, including physiological saline, other buffers, salts, etc. Alternatively, it is also possible to reconstitute the powder and use it to form liquid aerosols for delivery by inhalation.

The appropriate dosage ("therapeutically effective amount") of the biologically active material will depend, for example, on the condition to be treated, the severity and course of the condition, whether the biologically active material is administered for preventive or therapeutic purposes, previous therapy, the patient's clinical history and response to the biologically active material, the type of biologically active material used, and the discretion of the attending physician. The biologically active material can be suitably administered to the patent at one time, or over a series of treatments, and can be administered to the patent at any time from diagnosis onwards. The biologically active material can be administered as the sole treatment or in conjunction with other drugs, such as small molecule or chemically synthesized drugs, or therapies useful in treating the condition in question.

In a preferred embodiment, the spray freeze dried powder particles of the invention can be mixed with bulking agents or carriers. This is distinguishable from the use of bulking agents or carriers as formulation constituents during the spray freeze drying process in that these agents can be, e.g., powders interspersed with the freeze dried particles or adsorbed onto the particles. Mixed in or blended particle bulking agents or carriers can be used to reduce the concentration of the therapeutic agent in the powder being delivered to a patient; that is, it may be desirable to have larger volumes of material per unit dose. Bulking agents can also be used to improve the dispersibility of the powder within a dispersion device, and/or to improve the handling characteristics of the powder. Suitable bulking agents include, but are not limited to, lactose, mannitol, and hydroxyethyl starch (HES). Accordingly, bulking agents, if added, may be added in varying ratios, e.g., from about 1:800 to about 20:1 therapeutic agent to bulking agent, less than about 1:400, and from about 1:300 to about 1:200 being typically preferred, and from about 1:100 to about 1:200 being especially preferred.

Once made, the powders of the invention can be capable of being readily dispersed by an inhalation device and subsequently inhaled by a patient so that, e.g., the particles are able to deposit by contact or inertial impaction onto the pulmonary surfaces. Thus, the powders of the invention are formulated into unit dosages comprising therapeutically effective amounts of therapeutic agents, and used to deliver therapeutic agents to a patient, e.g., for the treatment of any number of disorders that are associated with the particular therapeutic agent. The dosage receptacle is one that fits within a suitable inhalation device to allow for the aerosolization of the powder formulation by dispersion into a gas stream to form an aerosol. These can be ampoules, capsules, foil pouches, blister packs, vials, etc. The container can be formed from any number of different materials, including plastic, glass, foil, etc. The container generally holds the spray-dried powder, and includes directions for use. The unit dosage containers can be associated with inhalers that can deliver the powder to the patient. These inhalers can optionally have chambers into which the powder is dispersed to produce a aerosol suitable for inhalation by a patient.

Additionally, the powder compositions of the invention can be further formulated in other ways, e.g., in the preparation of sustained release compositions, for example for implants, patches, etc. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., Biopolymers, 22, 547-556

[1983]), poly(2-hydroxyethyl methacrylate) (Langer et al., J. Biomed. Mater. Res., 15: 167-277 (1981), and Langer, Chem. Tech., 12: 98-105 [1982]), ethylene vinyl acetate (Langer et al., supra) or poly-D-(−)-3-hydroxybutyric acid (EP 133,988). The spray freeze dried powder can also be used to prepare a PROLEASE™ formulation of the therapeutic agent. Sustained-release compositions also include liposomally entrapped therapeutic agents. Liposomes containing therapeutic agents are prepared by methods known per se: DE 3,218,121; Epstein et al., Proc. Natl. Acad. Sci. U.S.A., 82: 3688-3692 (1985); Hwang et al., Proc. Natl. Acad. Sci. U.S.A., 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the optimal therapy.

As a general proposition, the therapeutically effective amount of the biologically active material administered can be in the range from less than about 0.1 ng/kg to about 50 mg/kg of patent body weight whether by one or more administrations, with the typical range of protein used being about 0.3 ng/kg to about 20 mg/kg, from about 20 ng/kg to about 1 mg/kg, from about 1 ug/kg to about 500 ug/kg, administered daily, for example. However, other dosage regimens may be useful. The progress of this therapy is easily monitored by conventional techniques.

The invention also encompasses methods which increase the "shelf-life" or storage stability of dried biologically active materials stored at elevated temperatures. Increased storage stability can be determined by recovery of biological activity in accelerated aging trials. The dry particle compositions produced by methods of the invention can be stored at any suitable temperature. Preferably, the compositions are stored at about −70° C. to about 80° C. More preferably, the compositions are stored at about 0° C. to about 60° C. Most preferably, the compositions are stored at ambient temperatures, e.g., about 25° C.

Compositions of the Invention

Compositions of the invention include, e.g., freeze dried powder particles prepared by a process of preparing a liquid formulation containing a bioactive material, spraying the formulation into a cold fluid to form frozen droplets, lyophilizing the droplets, annealing the droplets, and recovering freeze dried particles with an average physical size ranging from about 0.5 um to about 20 um. The freeze dried particles of bioactive material glassified in a polyol can have, e.g., an average physical diameter ranging from about 0.5 um to about 20 um, and have an average aerodynamic diameter ranging from about 1 um to about 10 um, or about 5 um. Bioactive material of the invention can be, e.g., viruses, bacteria, cells, liposomes, and/or the like.

Liquid Formulations for Preparation of Spray Freeze Dried Powder Particles

Dried powder particles of the invention can be prepared from liquid formulations containing, e.g., one or more bioactive material, polyol, polymer, an amino acid, surfactant, buffers, bulking agents, and/or the like. Such formulations can be processed according to methods of the invention to provide stable freeze dried powder particle compositions for storage and administration of the bioactive materials.

Bioactive materials in particles and formulations of the invention include, e.g., materials with detectable bioactivity in living systems, biological cells and molecules used in analysis, biological cells and molecules used in medicine, biological cells and molecules used in research, and/or the like. For example, bioactive materials of the compositions of the invention include bacteria, cells, liposomes, viruses, and/or the like.

Bioactive materials in the freeze dried particles of the invention can be, e.g., highly pure and/or active at the time of drying, due to the reduced shear stress, the low drying temperatures, and the short drying times used in their preparation. Bioactive materials are, e.g., stable in the freeze dried particles due to the low initial process degradation and the protective aspects of the composition excipients. Bioactive materials of the composition can be, e.g., reconstituted at high concentrations without degradation due to the high surface to volume ratio of the porous particles and the solubility enhancements provided by the excipients of the compositions.

Liquid formulations spray-dried to form the freeze dried particles of the invention contain, e.g., the bioactive materials of the invention in an amount ranging from less than about 1 pg/ml to about 150 mg/ml (15 weight percent), from less than about 1 ng/ml to about 100 mg/ml, or from about 10 ng/ml to about 50 mg/ml. Bioactive materials in the freeze dried particles of the invention are generally present in amounts ranging, e.g., from less than about 0.01 weight percent to about 80 weight percent, from about 40 weight percent to about 60 weight percent, or about 50 weight percent. Bioactive materials in reconstituted particles can have a concentration different from that of the original liquid formulation, e.g., in concentrations ranging from less than about 0.1 ng/ml to about 500 mg/ml, from about 1 ug/ml to about 400 mg/ml, or about 100 mg/ml.

Bioactive materials can include complex materials with lipid membranes, such as, e.g., biologically active, viable or non-living, cells, viruses, and/or liposomes. For example the bioactive materials can include vaccines, viruses, liposomes, bacteria, platelets, and cells. Viral bioactive agents can include, e.g., live and/or attenuated influenza virus, parainfluenza virus, human metapneumovirus, respiratory syncytial virus, herpes simplex virus, corona virus family members, cytomegalovirus, SARS virus, Epstein-Barr virus, their derivatives, and/or the like, which can be present in the liquid formulations of the invention in amounts ranging from less than about $10^3$ TCID$_{50}$/mL to about $10^{12}$ TCID$_{50}$/mL, or from about $10^6$ TCID$_{50}$/mL to about $10^9$ TCID$_{50}$/mL. Viral bioactive materials can generally be present in the liquid formulations in an amount of less than about 1%; more preferably, less than about 0.1%; and most preferably, less than about 0.05% by weight. Dried powder particle compositions of the invention can provide virus present in an amount, e.g., from about $10^1$ TCID$_{50}$/g to not more than about $10^{12}$ TCID$_{50}$/g. Dried powder particle compositions can provide virus present in an amount, e.g., of about $10^1$ TCID$_{50}$/g, about $10^2$ TCID$_{50}$/g, about $10^3$ TCID$_{50}$/g, about $10^4$ TCID$_{50}$/g, about $10^5$ TCID$_{50}$/g, about $10^6$ TCID$_{50}$/g, about $10^7$ TCID$_{50}$/g, about $10^8$ TCID$_{50}$/g, about $10^9$ TCID$_{50}$/g, about $10^{10}$ TCID$_{50}$/g, or about $10^{11}$ TCID$_{50}$/g.

Polyols of the invention can include, e.g., various sugars, carbohydrates, and alcohols. For example, the polyols can include non-reducing sugars, sucrose, trehalose, sorbose, melezitose, and/or raffinose. The polyols can include, e.g., fructose, mannose, maltose, lactose, arabinose, xylose, ribose, rhamnose, stachyose, galactose, glucose, mannitol, xylitol, erythritol, threitol, sorbitol, glycerol, L-gluconate, and/or the like. Where it is desired that the formulation be freeze-thaw stable, the polyol is preferably one which does not crystallize at freezing temperatures (e.g. −20° C.) such that it destabilizes the biologically active material in the formulation. The amount of polyol used in the liquid formulation can vary depending on the nature of the bioactive material, the type of polyol, and the intended use. However, generally, the final concentration of polyol is between about 1% and 40%; more preferably, between about 1% and 20%, between about 1% and 10%, or about 5% by weight. In a particularly preferred embodiment, the liquid formulation comprises about 5% sucrose.

Polymers of the invention can include, e.g., various carbohydrates, polypeptides, linear and branched chain hydrophilic molecules. For example, polymers of the formulation can include dextran, human serum albumin (HSA), nonhydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, or hydrolyzed gelatin, and/or the like. These polymers do not necessarily solely stabilize the biologically active material against inactivation; they also can help to prevent the physical collapse of the freeze-dried material during lyophilization and subsequent storage in the solid state. Preferably, hydrolyzed gelatin is used with a molecular weight of between about 1,000 Da and 50,000 Da, or about 3,000 Da. Generally, the concentration of polymer in a liquid formulation is, e.g., from about 0.5 to about 10%; more preferably, between about 1 and 5%.

Gelatin and more preferably, hydrolyzed gelatin, can be used as the polymer in compositions of the invention. "Hydrolyzed gelatin" refers to gelatin that has been subjected to partial hydrolysis to yield a partially hydrolyzed gelatin having a molecular weight of from about 1 kDa to about 50 kDa. This gelatin hydrolysis product has approximately the same amino acid composition as gelatin, but can be, e.g., less immunogenic. The typical amino acid composition of hydrolyzed gelatin is known. Partially hydrolyzed gelatin may be obtained from any number of commercial sources. Partially hydrolyzed gelatin may also be obtained by enzymatic hydrolysis of gelatin by means of a proteolytic enzyme, such as, for example, papain, chymopapain, and bromelin, although other known hydrolysis means may be employed, e.g., acid hydrolysis. Preferably, a gelatin having a molecular weight of between about 1 kDa and 50 kDa is used. The gelatin can be derived from a variety of sources, including pig and bovine. Humanized collagen, as well as highly processed collagen, for example, FreAlagin, a pharmaceutical gelatin with reduced allergenicity, available from Miyagi Chemical Industrial Co, Ltd., can be used. Again, the amount of gelatin used in the formulation will vary depending on the overall composition of the formulation and its intended use. Generally, the concentration of gelatin will be from about 0.5 to about 10%; more preferably, between about 1 and 5%. A preferred formulation comprises about 5% gelatin.

Liquid formulations for preparation of the compositions of the invention can include, e.g., one or more surfactants to aid in solubility and stability of formulation constituents. Surfactants can be present in formulations of the invention in a concentration ranging from about 0.001 weight percent to about 2 weight percent, or about 0.01 weight percent to about 1 weight percent. The surfactants can include, e.g., nonionic detergents, such as polyethylene glycol sorbitan monolaurate (Tween 20), polyoxyethylenesorbitan monooleate (Tween 80), block copolymers of polyethylene and polypropylene glycol (Pluronic), and/or the like.

Examples of suitable non-ionic surfactants are alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these, polyacrylates and acrylic acid graft copolymers. Other nonionic surfactants are known per se to those skilled in the art and have been described in the literature. Preferred substances are polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these. Particularly preferred surfactants include polymers of a mixture of polyoxyethylene and polyoxypropylene such as Pluronic F68 (available from BASF).

Examples of suitable ionic surfactants are alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, lignin-sulfite waste liquor, including their alkali metal, alkaline earth metal, ammonium and amine salts, alkyl phosphates, quaternary ammonium compounds, amine oxides, betaines, and mixtures of these. Preferred substances include Pluronic F68 or Pluronic F188 with polyoxyethylene sorbitan monolaurate (i.e., Tween 20, available from Sigma) being particularly preferred.

Buffers can be present, e.g., to control pH, enhance stability, affect constituent solubility, provide comfort on administration, and the like, in formulations for preparation of freeze spray dried particle compositions. Formulation pH can be controlled in the range from about pH 3 to about pH 10, from about pH 6 to about pH 8, from about pH 7 to about pH 7.4, or about pH 7.2. Preferred buffers are often paired acid and salt forms of a buffer anion generally recognized as safe for the particular route of administration of the bioactive material. Typical buffers for use in the formulations and compositions of the invention include, e.g., potassium phosphate, sodium phosphate, sodium acetate, histidine, imidazole, sodium citrate, sodium succinate, ammonium bicarbonate, carbonates, and the like. Generally, buffers are used at molarities from about 1 mM to about 2 M, with from about 2 mM to about 1 M being preferred, and from about 10 mM to about 0.5 M being especially preferred, and 25 mM to 50 mM being particularly preferred.

In one embodiment, the formulation contains the above-identified agents (i.e., biologically active material, polyol, surfactant, and gelatin) and is essentially free of one or more preservatives, such as benzyl alcohol, phenoly, m-cresol, chlorobutanol, and benethonium chloride). In another embodiment, a preservative may be included in the formulation, particularly when the formulation is a multidose formulation.

One or more pharmaceutically acceptable carriers, excipients, or stabilizers such as those described in Remington's Pharmaceutical Sciences 16$^{th}$ Edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; salt-forming counterions such as potassium and sodium; antioxidants, such as methionine, N-acetyl cysteine, or ascorbic acid; chelating agents, such as EDTA or EGTA. Amino acids, such as, e.g., arginine and methionine can be included in the formulations. Arginine can be present in the formulations in an amount ranging from about 0.1 weight percent to about 5 weight percent. Methionine can be present in the formulation in a concentration ranging from about 1 mM to about 50 mM or about 10 mM. Glycerol can be present in the formulation in a concentration ranging, e.g., from about 0.1 weight percent to about 5 weight percent, or about 1 weight percent. EDTA can be present in the formulation in a concentration ranging, e.g., from about 1 mM to about 10 mM, or about 5 mM.

Other drugs can be included in the compositions of the invention to, e.g., provide complimentary pharmacological or therapeutic effects. The other drugs can be additional bioactive materials, small molecule drugs, chemically synthesized drugs, extracted drugs, and/or the like. For example, the other drugs optionally included in compositions of the invention can be adjuvants, analgesics, anesthetics, antiseptics, antibiotics, vasodilators, decongestants, coagulants, and/or the like.

Freeze Dried Powder Particles

The compositions of the invention include freeze dried powder particles that, e.g., show good dispersibility, physical stability, and/or chemical stability of bioactive materials. The particles can be prepared, e.g., by spraying a liquid formulation into a cold fluid to form frozen droplets, and lyophilizing the droplets to form stable freeze dried particles. The particles can have a smaller aerodynamic size than physical size with a bioactive material protected in a porous glassy matrix. For example, A live virus can be stabilized in a dried particle composition containing about 40 weight percent sucrose, about 5 weight percent gelatin, and about 0.02 weight percent block copolymer of polyethylene and polypropylene glycol by weight.

The spray freeze dried powders of the invention can be characterized, e.g., on the basis of their average particle size. Preferably, the average aerodynamic particle size ranges from about 0.5 um to about 20 um, with from about 1 um to about 10 um being more preferred and from about 3 um to about 5 um being especially preferred. A preferred average particle size is less than 10 μm. The average physical particle size of the powder can be measured as mass mean diameter (MMD) by convention techniques. The aerodynamic diameter can be measured, e.g., using an Aerosizer (Model 3225 Aerosizer® DSP Particle Size Analyzer by TSI Inc.) or approximated by multiplying the geometric particle diameter (obtainable from laser diffraction particle analyzers) to the square root of the bulk density of the powder.

Compositions of freeze dried particles in the invention can include, e.g., a bioactive material glassified in a porous matrix providing particles with an average aerodynamic size ranging from about 0.5 um to about 10 um, but with an average physical diameter ranging from about 0.5 um to about 20 um. Physical and chemical stability is commonly enhanced by the presence of, e.g., sucrose and/or trehalose in an amount ranging from about 10% to about 95% of the particles by weight. The freeze dried particles can protect the bioactive material to provide stability, e.g., for more than about 1 year in storage at about 25° C. (see, FIG. 2) and/or for about two or more years in storage at 4° C.

The powder particles of the invention can be characterized on the basis of their moisture content. This moisture content is generally below about 15% water by weight, with less than about 10% being preferred, and less than about 5% being particularly preferred. In a preferred embodiment, the particles are dry with a moisture content of from about 1% to about 5%. The moisture content of particles of a dry powder may be measured using a Karl Fisher moisture analyzer, loss-on-drying moisture balances, DSC, or by thermogravimetric analyzers.

Figure 5A:
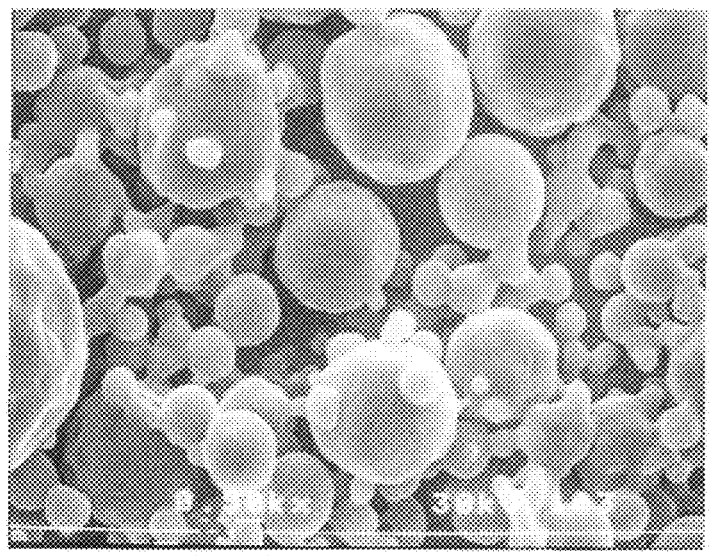
FIG. 5 shows Scanning Electron Micrographs of spray-freeze powder
Figure 5B:
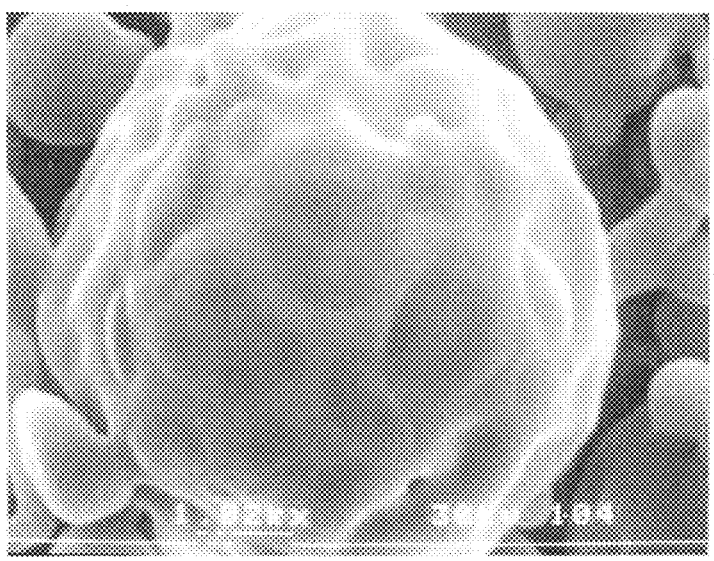

In addition to the above characteristics, the particles can be characterized on the basis of their general morphology as well. In general, particles made by the processes of the invention are generally spherical and porous (see, FIG. 5). The particles of the invention can have a density less than 1, e.g., less than about 0.9, less than about 0.7, less than 0.4, or less than 0.2 g/cm$^3$; or between about 0.5 and 0.2 g/cm$^3$.

Figure 3:
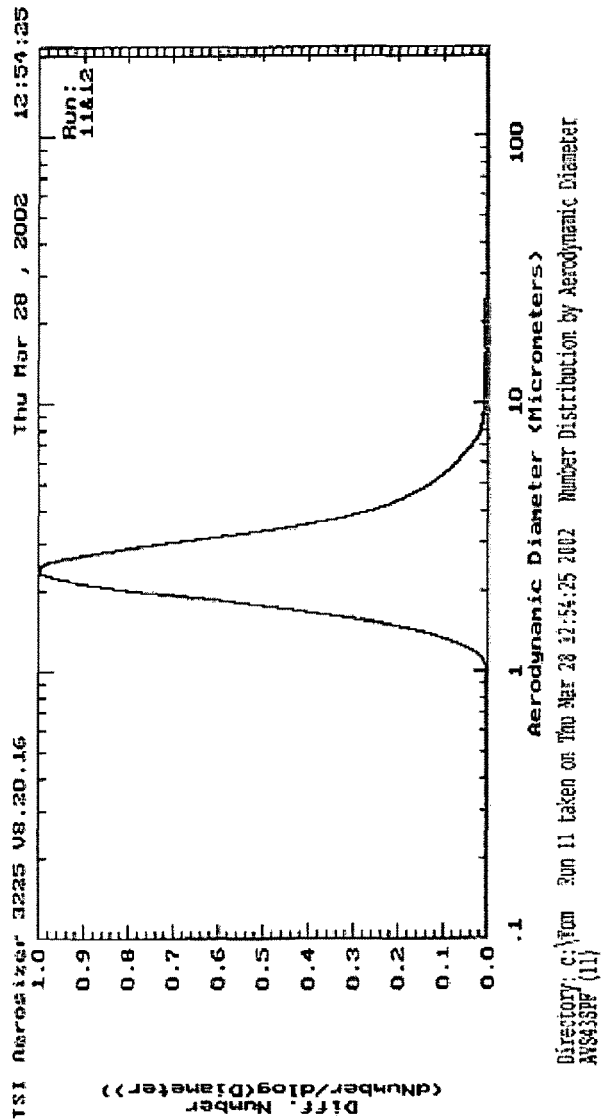
FIG. 3 shows the aerodynamic particle size distribution of AVS43SF powder.
Figure 4:
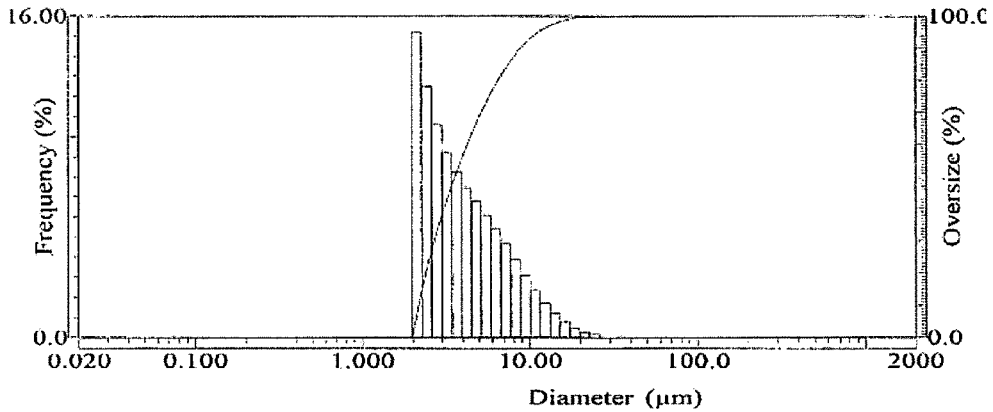
FIG. 4 shows a physical particle size distribution of AVS43SF spray-freeze powder.

Exemplary aerodynamic and physical particle size analyses of spray freeze dried powder of the invention are shown in FIG. 3 and FIG. 4, respectively. FIG. 3 shows acquired data and a chart of the number of particles versus the aerodynamic diameter of the particles for formulation AVS43SF as determined using an Aerosizer Model 3225 particle size analyzer. Note the average aerodynamic size of AVS43SF freeze dried particles is about 2.5 um and the density 0.50 g/c$^3$. FIG. 4 shows acquired data and a chart of the frequency of particles at a range of physical particle diameters as determined using a Horiba® Model LA-920 laser defraction particle size analyzer. Note the average physical diameter of AVS43SF freeze dried particles was determined to be about 4.7 um. An electron micrograph of AVS43SF freeze dried particles is presented in FIG. 5.

Figure 6:
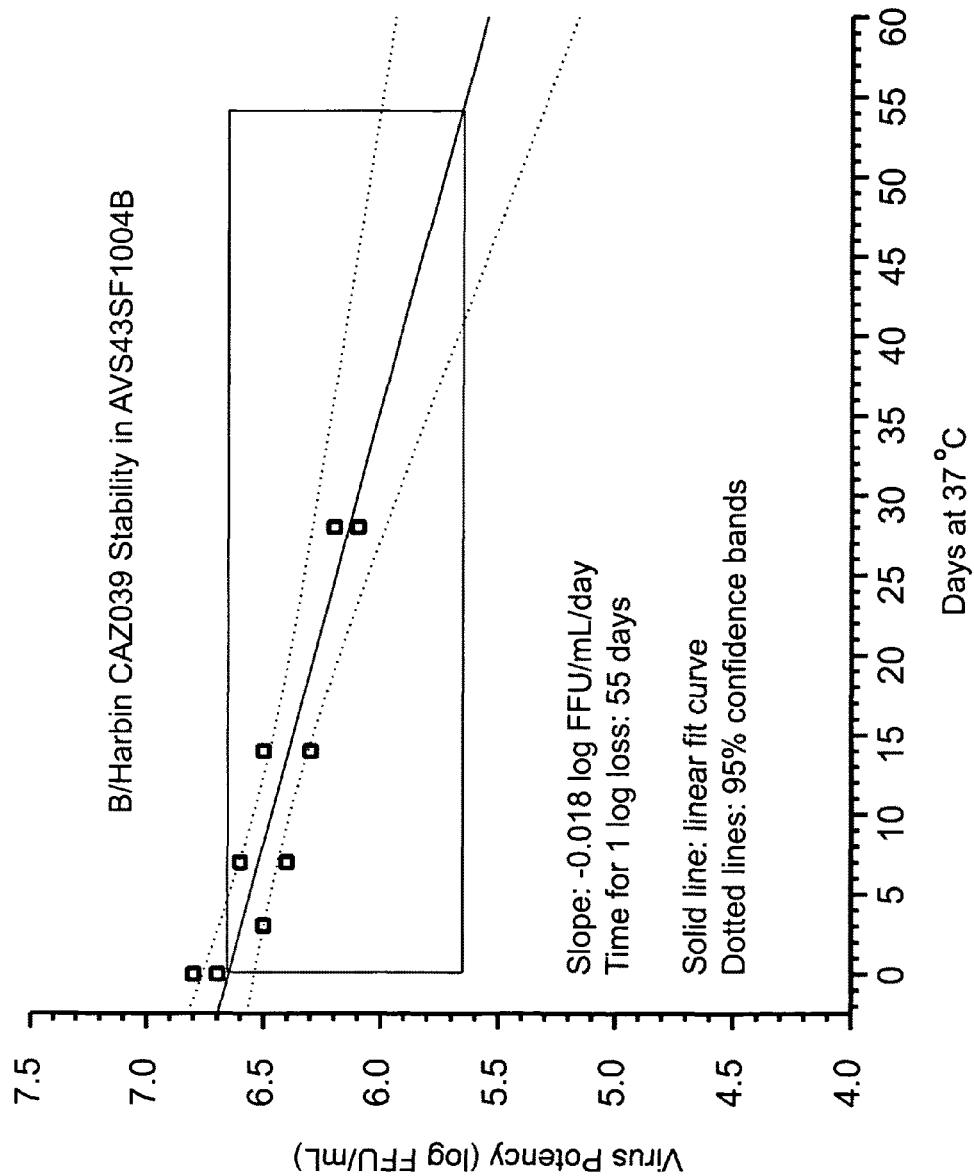
FIG. 6 shows the stability of influenza virus B/Harbin which has been formulated as AVS43SF. The time for 1 log loss in virus potency at 37° C. is 55 days.

The freeze dried particles of the invention can be stable, i.e., they retain their biological activity, chemical and/or physical properties. Stability can be measured by analysis of relevant parameters after storage of the particles at a selected temperature for a selected time period. As will be appreciated by those in the art, the length of time and the conditions under which a product can be stable will depend on a number of factors, including the types of excipients, ruggedness of the bioactive material, and the storage conditions (such as, temperature, relative humidity, exposure to light, etc.). Generally, for rapid screening, a matrix of conditions are run and inferences made using analyses bases on Arrhenius kinetics or other trend analyses. Commonly, product formulations are tested, e.g., at 2-8° C., 25° C. and 37° C., for periods of 2, 12 and 52 weeks. Calculations based on Arrhenius kinetics using data from accelerated stability studies (such as 37° C. stability studies of virus potency, as shown in FIGS. 6 and 7) can provide estimates of expected potency at future times and/or expected potency after storage at lower temperatures. These tests can be carried out in controlled humidity environments, such as 38% relative humidity (rh), as is outlined in the Examples. Thus, in a preferred embodiment with a viral bioactive material, the powders of the invention preferably lose less than about 2 logs of their biological activity over 12 months at 25° C. storage condition, with losses of less than about 1.5 log being preferred and less than about 1.0 log being especially preferred. For live influenza viruses, in a preferred embodiment, the powders of the invention preferably lose less than about 2 log FFU/ml of their biological activity over 18 months, with losses of less than about 1.5 log FFU/ml being preferred, and less than about 1.0 log FFU/ml being especially preferred.

The invention also encompasses methods of increasing the "shelf-life" or storage stability of dried bioactive materials stored at elevated temperatures. Storage stability can be evaluated by monitoring trends in stability indicating parameters, such as biological activity, in accelerated aging trials followed by predictive analysis based on Arrhenius kinetics. The composition can be stored at any suitable temperature for stability studies. Preferably, the compositions are stored at about 0° C. to about 80° C. More preferably, the compositions are stored at about 20° C. to about 60° C. Most preferably, the compositions can stored at or above ambient temperatures and yet provide adequate biomaterial strength and quality for a suitable period of time.

In a preferred embodiment, the dry powders of the invention retain dispersibility over time. Generally, this is quantified by the retention of a high FPF (fine particle fraction) over time; that is, the powder minimally aggregates, cakes or clumps over time. FPF can be determined by the use of an Anderson cascade impactor and is generally know to those in the art. Similarly, when dispersibility is being evaluated, the powders of the invention lose less than about 50% of their FPF, with losses of less than about 30% being preferred, and losses of less than about 20% being especially preferred.

The present invention includes an article of manufacture comprising, e.g., a container containing freeze dried particles prepared by spray freeze drying a liquid formulation of bioactive material, a polyol, an amino acid additive, a polymer additive, and a surfactant. In an embodiment of the invention, an article of manufacture is provided comprising a container which holds the pharmaceutical formulation of the present invention and optionally provides instructions for its use. Suitable containers include, for example, bottles, ampoules, vials, blister packs, syringes, and/or the like. The container can be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The freeze dried particles described herein can be stable, i.e., they retain their biological activity, and are chemically and/or physically stable. The freeze dried particles were tested for stability by subjecting them to aging at elevated temperature (e.g., accelerated stability studies at 37° C. or more) and measuring their biological activity, chemical and/or physical stability. Results of these studies demonstrate that these particles which were dried at 35° C. using the methods of the invention were stable for at least 1 year at 25° C. Such freeze dried particles are stable even when high concentrations of the biologically active material are used. Thus, these dry particles are advantageous in that they may be shipped and stored at temperatures at or above room temperature for long periods of time.

Apparatus of the Invention

The apparatus of the invention can include, e.g., a spray chamber and/or a drying chamber. The spray chamber can have, e.g., a mounted spray nozzle for spraying liquid formulation into a cold fluid. The spray chamber can act as a drying chamber, or optionally, a separate drying chamber can be provided. The drying chamber can provide, e.g., outlets to a vacuum pump and/or ports to circulate drying gasses.

As shown, for example, in FIG. 1, a spray/freeze chamber can comprise, e.g., spray nozzle 10 directing spray mist of droplets 11 into cold fluid 12. Virus suspension 13 can be pumped from a liquid formulation holding container 14 through a conduit to the spray nozzle. After a batch of frozen droplets has been prepared, the cold fluid can be decanted or evaporated away to leave the frozen droplets in the chamber for lyophilization (drying) and/or collection (recovery).

The liquid formulation holding container can be pressurized, and/or pumps can be employed in the conduit, to deliver liquid formulations to the nozzle. The rate of delivery can be controlled by means commonly practiced in the art, such as, e.g., by controlling the pumping rate or by controlling valves in the conduits. The pumps can be any type known in the art, such as, e.g., peristaltic pumps, rotary pumps, diaphragm pumps, piston pumps, and the like. Valves can be any appropriate style known in the art, including, e.g., ball and seat, diaphragm, needle, that can restrict the flow of pressurized fluids.

The nozzle can include, e.g., an outlet orifice through which the liquid formulation is sprayed. The size of the outlet orifice internal diameter can affect the size of droplets produced in the spray; with larger droplets (and ultimately, particles) formed by spraying from larger outlets. Typically, the orifice has, e.g., an internal diameter from less than about 50 um to about 500 um, about 50 um to about 200 um, or about 100 um.

A drying chamber can be provided to hold frozen droplets for exposure to lyophilization and/or secondary drying conditions. The drying chamber can be the spray/freeze chamber to allow continued processing without having to collect the droplets for transfer to a dedicated chamber specialized in drying. The drying chamber can be adapted to provide controlled temperature, humidity and/or gas pressure conditions selected for lyophilization and/or secondary drying. The drying chamber can include, e.g., an outlet to a vacuum pump capable of evacuating gasses from the chamber to provide the required vacuum (e.g., less than about 400 mTorr, or 200 mTorr, or less) during lyophilization and secondary drying. The drying chamber can include, e.g., inlet and outlet ports for circulation of a warm dry gas during secondary drying. The drying chamber can include, e.g., a temperature controlled surface to provide heat to particles in contact with the surface during lyophilization and/or secondary drying. The drying chamber can be adapted, e.g., to provide a cyclonic vortex or fluidized bed where particles can be suspended in drying gasses during drying or application of sustained release polymer coats to the particles.

The spray/freeze chamber and/or drying chamber can be adapted to provide a collection vessel, e.g., Lyogard™ tray, for collection freeze dried particles. For example, droplets or particles can settle to a removable vessel at the bottom of the chamber where they can accumulate to be recovered for further processing, use, packaging, or storage.

EXAMPLES

The following examples are offered to illustrate, but not to limit the claimed invention.

Example 1

Spray Freeze Drying Influenza Formulations

In the following examples, liquid formulations were sprayed into liquid nitrogen through a spray nozzle with a 150 um internal diameter orifice. With reference to the table below, the frozen droplets were lyophilized to the listed moisture contents to obtain the listed stability (days to 1 log loss).

Processing materials included influenza virus lot number CAIV, liquid nitrogen (Praxair) as the cold fluid for freezing, and nitrogen atomizing gas, grade 4.8. Hardware included an ISCO, Model 250D syringe pump to feed the liquid formulation, a Sierra 1 L/min mass flow meter to monitor flow of the atomizing gas, and a custom made stainless steel effervescence atomizing spray nozzle.

The liquid formulation was sprayed at 2 mL/min through the nozzle and atomized by nitrogen gas at 1 L/min, into a container of liquid nitrogen. Nozzle liquid formulation feed rates up to 30 mL/min have been achieved with similar results. After spraying, a slurry of frozen droplets was poured into glass vials and transferred into a lyophilizer (drying chamber). Cold liquid nitrogen fluid was dispersed by evaporation to leave the frozen particles in the vials. After lyophilization, resultant freeze dried powder particles were characterized by particle size, moisture content, process loss, and stability. Particle size was adjusted appropriately to optimize powder for intranasal or pulmonary administration. The adjustment of particle and aerodynamic size ranges can be made by changing the solids content of the liquid feed, changing the liquid droplet size and the liquid feed rate, changing the annealing conditions during primary drying, changing the type of excipient used, as well as usage of secondary size reduction steps such as jet milling, mechanical impact milling, fluidized bed drying, spray coating, etc.

The following liquid formulations were prepared with influenza virus as the bioactive material:

AVO47=5% sucrose, 2% trehalose, 10 mM methionine, 1% arginine, 0.2% Pluronic F68, 50 mM KPO4, pH 7.2

AVS43=40% sucrose, 5% gelatin, 10 mM methionine, 0.02% Pluronic F68, 25 mM KPO4, pH 7.2

AVS53=40% sucrose, 5% gelatin, 0.02% Pluronic F68, 25 mM KPO4, pH 7.2

The liquid formulations were subjected to spray freeze drying as generally described above with the modifications set forth in the table below to yield particles with the following characteristics:

| Formulation | Run Notes | % Moisture* | Days to 1 log loss @ 37° C. |
|---|---|---|---|
| AV047 SF0911 | Test run, vials, cycle 1 | 1.56 KF | −16.7 |
| AV047 SF0914V | Cycle 1, vials | 1.33 KF | |
| AV047 SF0914B | Cycle 1, Lyogard ™ tray | | −17.7 |
| AV047 SF0917V | Cycle 1, vials | 1.64 KF | −15.3 |
| AV047 SF0917B | Cycle 1, Lyogard ™ tray | 2.51 KF | 21.0 |
| AVS43 SF1004V | Cycle 2, vials, Buchi Nozzle | 2.52 KF | 33.3 |
| AVS43 SF1004B | Cycle 2, Lyogard ™ tray, Buchi Nozzle | | 54.5 See FIG. 3 |
| AVS43 SF1008V | Cycle 2, vials, Buchi Nozzle, AVS43 half-strength | 0.82 KF | 15.6 |
| AVS43 SF1008B | Cycle 2, Lyogard ™ tray, Buchi Nozzle, AVS43 half-strength | 0.87 KF | 13.9 |
| SF01V | Cycle 2 (23 hr), vials, Buchi Nozzle, AVS43 w/o Gelatin (AVS51) | 2.8 KF | 13.5 |
| SF01T | Cycle 2, Lyogard ™ tray, Buchi Nozzle, AVS43 w/o Gelatin (AVS51) | 0.51 FD | 19.2 |
| AVS53 SF1V | Cycle 3, vials, Buchi Nozzle, AVS43 w/o Methionine (AVS53) | 1.74 FD | 66.7 |
| AVS53 SF1T | Cycle 3, Lyogard ™ tray, Buchi Nozzle, AVS43 w/o Methionine (AVS53) | 1.53 FD | 35.7 |
| AVS43 SF3aV | Cycle 2 (23 hr), vials, Buchi Nozzle | 2.84 KF | 29.1 |
| AVS43 SF3aT | Cycle 2, Lyogard ™ tray, Buchi Nozzle | 2.62 KF | 40.8 |
| AVS4 3SF3bV | Cycle 2, vials, Buchi Nozzle, 30 min @ 15° C. prior to spraying | 3.15 KF | 31.9 |
| AVS43 SF4aV | Cycle 3 (16 hr), vials, Buchi Nozzle | 6.11 KF | 41.9 |
| AVS43 SF4aT | Cycle 3, Lyogard ™ tray, Buchi Nozzle | 1.82 KF | 38.4 |
| AVS43 SF4bV | Cycle 3, vials, Buchi Nozzle, 30 min @ 15° C. prior to spraying | 5.21 KF | 42.2 See FIG. 2 |

*KF is moisture content determined by the Karl Fisher method, FD is moisture content determined by the loss-on-drying method.

Example of Lyophilization Cycle:

| Cycle | Temp (° C.) | Time (minutes) | Vac (mTorr) | Ramp/Hold |
|---|---|---|---|---|
| SF Cycle 2 | −40 | 15 | 250 | H |
| | −25 | 45 | 250 | R |
| | −25 | 720 | 250 | H |
| | 35 | 240 | 250 | R |
| | 35 | 360 | 250 | H |

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, the formulations, techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of preparing a spray freeze-dried composition of particles comprising a bioactive material for pulmonary administration, which method comprises:
   providing a liquid formulation comprising the bioactive material and one or more polyols;
   spraying the liquid formulation comprising the bioactive material to form droplets;
   freezing the droplets by immersion into a cold fluid;
   drying said droplets under conditions adapted to form powder particles comprising the bioactive material in a glassy matrix; and,
   recovering the particles;
   wherein the bioactive material comprises a virus, bacteria, a non-living cell, or liposomes, and wherein the powder particles are characterized by an average physical size ranging from about 0.5 um to about 20 um.

2. The method of claim 1, further comprising annealing the frozen droplets.

3. The method of claim 1, wherein the virus comprises influenza virus, parainfluenza virus, human metapneumovirus, respiratory syncitial virus, corona virus family members, herpes simplex virus, SARS virus, cytomegalo virus, or Epstein-Barr virus.

4. The method of claim 1, wherein the particles range in average aerodynamic size ranging from about 0.5 um to about 10 um.

5. The method of claim 1, wherein the particles comprise an average aerodynamic size of about 3 um.

6. The method of claim 1, wherein spraying comprises flowing a liquid formulation through a multifluid atomization assembly, a high pressure nozzle, or an ultrasonic nozzle.

7. The method of claim 1, wherein the liquid formulation comprises a polymer or a surfactant.

8. The method of claim 1, wherein the polyol is selected from the group consisting of sucrose, trehalose, sorbose, melezitose, stachyose, raffinose, mannitol, xylitol, erythritol, threitol, sorbitol, glycerol, fructose, mannose, maltose, lactose, arabinose, xylose, ribose, rhamnose, galactose, glucose, and L-gluconate.

9. The method of claim 7, wherein the polymer comprises dextran, human serum albumin (HSA), nonhydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, or hydrolyzed gelatin.

10. The method of claim 7, wherein the surfactant comprises a polyethylene glycol sorbitan monolaurate, a polyoxyethylenesorbitan monooleate, a block copolymer of polyethylene and polypropylene glycol.

11. The method of claim 1, wherein the cold fluid is a gas or liquid and comprises argon, carbon dioxide, air, or nitrogen.

12. The method of claim 11, wherein the cold fluid comprises a temperature ranging from about −40° C. to about −200° C.

13. The method of claim 1, wherein the liquid droplets comprise an average diameter ranging from about 0.5 um to about 20 um.

14. The method of claim 13, wherein the liquid droplets comprise an average diameter ranging from about 1 um to about 10 um.

15. The method of claim 1, wherein annealing comprises raising an annealing temperature of the frozen droplets to less than about a glass transition temperature of the frozen droplets.

16. The method of claim 15, wherein the annealing temperature comprises a temperature less than about −10° C.

17. The method of claim 1, wherein drying the droplets comprises applying a vacuum to the droplets, thereby forming powder particles.

18. The method of claim 17, wherein the vacuum comprises a pressure of less than about 400 mTorr.

19. The method of claim 1, wherein drying comprises adjusting the droplets to a drying temperature ranging from about 0° C. to about 50° C.

20. The method of claim 19, wherein drying further comprises primary drying at a temperature of less than about the glass transition temperature of the liquid formulation.

21. The method of claim 19, wherein drying further comprises a secondary drying at a temperature of about 35° C.

22. The method of claim 1, further comprising diafiltering, ultrafiltering, concentrating, or buffer exchanging the liquid formulation.

23. The method of claim 22, wherein the concentrating provides the bioactive material in the liquid formulation at a concentration ranging from about 5 mg/ml to about 75 mg/ml.

24. The method of claim 1, further comprising administering the powder particles to a mammal in a therapeutically effective amount.

25. The method of claim 24, wherein the effective amount ranges from about 0.1 ng/kg to about 50 mg/kg.

26. The method of claim 24, wherein administering comprises reconstituting and injecting the powder particles.

27. The method of claim 1, wherein the particles range in average aerodynamic size ranging from about 1 um to about 7 um.

28. The method of claim 1, wherein the particles are characterized by a particle density of 0.4 g/cm$^3$ or less.

29. The method of claim 1, wherein the bioactive material comprises a virus, bacteria, or a non-living cell.

* * * * *